United States Patent [19]

Faustini et al.

[11] Patent Number: 4,585,791
[45] Date of Patent: Apr. 29, 1986

[54] FURYL DERIVATIVES OF 16-SUBSTITUTED PROSTAGLANDINS

[75] Inventors: Franco Faustini, Milan; Achille Panzeri, Merate; Fabrizio Orzi, Milan; Enrico di Salle, Milan; Roberto Ceserani, Milan, all of Italy

[73] Assignee: Farmitalia Carlo Erba, S.p.A., Milan, Italy

[21] Appl. No.: 667,367

[22] Filed: Nov. 1, 1984

[30] Foreign Application Priority Data

Nov. 4, 1983 [GB] United Kingdom ............... 8329559

[51] Int. Cl.[4] .................. A61K 31/34; C07D 307/54
[52] U.S. Cl. ............................... 514/471; 514/222;
514/233; 514/234; 514/236; 514/255; 514/326;
514/336; 514/461; 514/473; 544/58.4; 544/152;
544/379; 546/214; 546/283; 549/473; 549/478;
549/479; 549/496; 549/501
[58] Field of Search .............. 549/473, 478, 479, 496,
549/501; 546/283, 214; 544/58.4, 152, 379;
514/222, 233, 234, 236, 255, 326, 336, 461, 471,
473

[56] References Cited

U.S. PATENT DOCUMENTS 3,956,284  5/1976  Pfizer ........................... 549/501 X

FOREIGN PATENT DOCUMENTS

| 2825855 | 12/1978 | Fed. Rep. of Germany . |
| A2394539 | 1/1979 | France . |
| A2517302 | 6/1983 | France . |
| 7306030 | 6/1973 | Netherlands . |
| 7309792 | 1/1974 | Netherlands . |
| 1446341 | 8/1976 | United Kingdom . |
| 2009145B | 8/1982 | United Kingdom . |

*Primary Examiner*—Richard L. Raymond
*Attorney, Agent, or Firm*—Murray and Whisenhunt

[57] ABSTRACT

The present invention relates to new furyl derivatives of 16-substituted prostaglandins, to a process for their preparation and to pharmaceutical and veterinary compositions containing them.

The new compounds of the invention are optically active or racemic prostaglandins of the following formula (I)

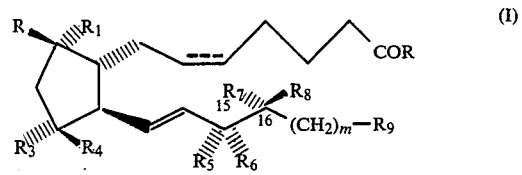

wherein
R is
(1) —OH or —OR' wherein R' is $C_1$–$C_6$ alkyl optionally substituted by phenyl or by a monocycloalkyl group or by a pentatomic or hexatomic heteromonocyclic ring containing at least one heteroatom chosen from O, S and N;
(2)

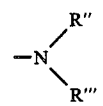

wherein each of R'' and R''', is independently, hydrogen; $C_1$–$C_6$ alkyl; phenyl; or a pentatomic or hexatomic heteromonocyclic ring containing at least one heteroatom chosen from O, S and N; or R'' and R''', together with the nitrogen atom to which they are linked, form a pentatomic or hexatomic heteromonocyclic ring optionally containing a further heteroatom chosen from O, S and N;
(3) —W—$(CH_2)_n$—X wherein W is —O— or —NH—, n is an integer of 1 to 4 and X represents a group —OR' or a group

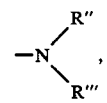

wherein
R', R'' and R''' are as defined above;
one of $R_1$ and $R_2$ is hydrogen and the other is hydroxy or
$R_1$ and $R_2$, taken together, form an oxo group;
one of $R_3$ and $R_4$ is hydrogen and the other is hydroxy;
one of $R_5$ and $R_6$ is hydroxy and the other is hydrogen, $C_1$–$C_6$ alkyl, $C_2$–$C_6$ alkenyl, $C_2$–$C_6$ alkynyl, or phenyl;
one of $R_7$ and $R_8$ is hydrogen and the other is a $C_1$–$C_4$ alkyl or tri-halo-$C_1$–$C_4$ alkyl group;
m is an integer of 1 to 3;
$R_9$ is a 2-furyl or 3-furyl group, optionally substituted by one or more substituents chosen from $C_1$–$C_4$ alkyl, $C_1$–$C_4$ alkoxy, tri-halo-$C_1$–$C_4$ alkyl and halogen; and the symbol ≅ represents a single bond or a cis double bond.

12 Claims, No Drawings

FURYL DERIVATIVES OF 16-SUBSTITUTED PROSTAGLANDINS

The invention includes also the pharmaceutically or veterinarily acceptable salts of the compounds of formula (I) as well as all the possible isomers of formula (I), e.g. the optical antipodes, i.e. the enantiomers, and the racemic mixtures of the optical antipodes, the geometric isomers and their mixtures, the epimers and their mixtures, and the mixtures of the diastereoisomers.

In this specification the alkyl, alkenyl and alkynyl groups, as well as the aliphatic moieties of the alkoxy groups, may be branched or straight chain.

A $C_1$-$C_6$ alkyl group is, preferably, methyl, ethyl, n-propyl or tert-butyl.

A $C_1$-$C_4$ alkyl group is, preferably, methyl or ethyl.

A $C_2$-$C_6$ alkenyl group is, preferably, vinyl or allyl.

A $C_2$-$C_6$ alkynyl group is, preferably, ethynyl or propargyl.

A $C_1$-$C_4$ alkoxy group is, preferably, methoxy or ethoxy.

A tri-halo-$C_1$-$C_4$ alkyl group is, preferably, a tri-halomethyl group, trifluoromethyl in particular.

A halogen is, preferably, chlorine or bromine.

When, with reference to the definitions reported above for the formula (I) substituents, R' represents a $C_1$-$C_6$ alkyl substituted by a monocycloalkyl group, this is, preferably, a $C_3$-$C_7$ monocycloalkyl, in particular cyclopentyl or cyclohexyl.

When R', or one of R" and R'", represents a $C_1$-$C_6$ alkyl group substituted by a pentatomic or hexatomic heteromonocyclic ring as reported above, the heteromonocyclic is, for example, furyl, tetrahydrofuryl, or pyridyl.

When R" and R'", together with the nitrogen atom to which they are linked, form a pentatomic or hexatomic heteromonocyclic ring as defined above, this is, preferably, morpholino, thiomorpholino, piperidino or piperazino.

When $R_7$ or $R_8$ is a $C_1$-$C_4$ alkyl group, this is, preferably, methyl or ethyl.

When $R_7$ or $R_8$ is a tri-halo-$C_1$-$C_4$-alkyl group, this is, preferably, trifluoromethyl.

When $R_7$ is a $C_3$-$C_7$ monocycloalkyl group, this is, preferably, a $C_5$-$C_7$ monocycloalkyl, in particular cyclopentyl or cyclohexyl.

Preferably in the above formula (I) R is (1) —OH; —OR' wherein R' is unsubstituted $C_1$-$C_6$ alkyl, in particular methyl or ethyl; (2)

wherein each of R" and R'" is, independently, hydrogen or $C_1$-$C_6$ alkyl, in particular methyl or ethyl; or (3) —W—$(CH_2)_n$—X wherein W is —O—, n is 2 and X is —OR' with R' as herein before defined.

Preferably $R_1$ is hydroxy and $R_2$ is hydrogen, or $R_1$ and $R_2$, taken together, form an oxo group; $R_3$ is hydroxy and $R_4$ is hydrogen; and one of $R_5$ and $R_6$ is hydroxy and the other is hydrogen.

Preferably one of $R_7$ and $R_8$ is hydrogen and the other is $C_1$-$C_4$ alkyl, m is 1, and $R_9$ is a 2-furyl group optionally substituted as reported above.

Pharmaceutically or veterinarily acceptable salts of the compounds of formula (I) are either the salts with both inorganic and organic pharmaceutically or veterinarily acceptable bases, or the salts with both inorganic and organic pharmaceutically or veterinarily acceptable acids. Inorganic bases are, for example, alkali metal, e.g. sodium or potassium, or alkaline earth metal, e.g. calcium or magnesium, hydroxides.

Organic bases are, for example, ammonium hydroxide and aliphatic or aromatic amines such as; for instance, triethylamine, trimethylamine, aniline and toluidine. Inorganic acids are, for example, hydrochloric, hydrobromic, sulphuric and phosphoric acid, and organic acids, are, e.g., glycolic, lactic, oxalic, malonic, malic, maleic, tartaric, citric, fumaric, cinnamic, mandelic, salicyclic, methanesulfonic and p-toluenesulfonic acid.

In the formulae of this specification a dashed line (ııııı) refers to a ring substituent in the α-configuration, i.e. to a substituents below the plane of the ring, and a wedged line (◄) refers to a ring substituent in the β-configuration, i.e. to a substituent above the plane of the ring. Similarly dashed lines (ııııı) and wedges lines (◄) indicate chain substituents in the α- and, respectively, in the β-configuration. A wavy line (∼) indicates that a substituent may be in the α- or in the β-configuration or both. Consequently, where a formula has a substituent with a wavy line bond, the formula may represent a compound having the substituent solely in the α-configuration or solely in the β-configuration, or the formula may represent a mixture of both compounds having the substituent in the α-configuration and compounds having the substituent in the β-configuration. Furthermore, the absolute "R" or "S" configurations of the chiral centers are assigned according to the sequence-rule procedure of IUPAC for the Nomenclature of Organic Chemistry (J.O.C. 35.9 2849, 1970).

A preferred class of compounds of the invention are the compounds of formula (I) wherein R is (1) hydroxy or OR' wherein R' is $C_1$-$C_6$ alkyl; or (2)

wherein each of R" and R'" is, independently, hydrogen or $C_1$-$C_6$ alkyl; or (3) —W—$(CH_2)_n$—X wherein W is —O—, n is 2 and X is OR' wherein R' is $C_1$-$C_6$ alkyl;

one of $R_1$ and $R_2$ is hydrogen and the other is hydroxy or $R_1$ and $R_2$, taken together, form an oxo group;

one of $R_3$ and $R_4$ is hydrogen and the other is hydroxy;

one of $R_5$ and $R_6$ is hydrogen and the other is hydroxy;

m is 1;

one of $R_7$ and $R_8$ is hydrogen and the other is $C_1$-$C_4$ alkyl;

$R_9$ is 2-furyl optionally substituted by a $C_1$-$C_4$ alkyl or $C_1$-$C_4$ alkoxy or tri-halo-$C_1$-$C_4$-alkyl group, and the symbol ═ represents a single bond or a cis-double bond;

and the pharmaceutically or veterinarily acceptable salts thereof.

A particularly preferred class of compounds of the invention are the compounds of formula (I) wherein
R is —OH or OR' wherein R' is $C_1$-$C_4$ alkyl;
$R_1$ and $R_2$, taken together, form an oxo group;
$R_3$ is hydroxy and $R_4$ is hydrogen;
one of $R_5$ and $R_6$ is hydrogen and the other is hydroxy;
m is 1;
one of $R_7$ and $R_8$ is hydrogen and the other is $C_1$-$C_4$ alkyl;
$R_9$ is unsubstituted 2-furyl, and
the symbol $\rightleftharpoons$ represents a single bond or a cis-double bond;
and the pharmaceutically or veterinarily acceptable salts thereof.

In the above particularly preferred class of compounds of the invention, when R is a group OR' it is, preferably, —OCH$_3$ or —O—C$_2$H$_5$; and the $C_1$-$C_4$ alkyl group represented by one of $R_7$ and $R_8$ is, preferably, methyl.

Specific examples of preferred compounds of the invention are:
5Z,13E-9α,11α,15S-trihydroxy-16S-methyl-18,19,20-trinor-17-(2'-furyl)-prosta-5,13-dienoic acid;
5Z,13E-9α,11α,15S-trihydroxy-16R-methyl-18,19,20-trinor-17-(2'-furyl)-prosta-5,13-dienoic acid;
5Z,13E-9α,11α,15S-trihydroxy-16S-methyl-18,19,20-trinor-17-(3'-furyl)-prosta-5,13-dienoic acid;
5Z,13E-9α,11α,15S-trihydroxy-16R-methyl-18,19,20-trinor-17-(3'-furyl)-prosta-5,13-dienoic acid;
5Z,13E-9-oxo-11α,15S-dihydroxy-16S-methyl-18,19,20-trinor-17-(2'-furyl)-prosta-5,13-dienoic acid;
5Z,13E-9-oxo-11α,15S-dihydroxy-16R-methyl-18,19,20-trinor-17-(2'-furyl)-prosta-5,13-dienoic acid;
13E-9-oxo-11α,15S-dihydroxy-16S-methyl-18,19,20-trinor-17-(2'-furyl)-prosta-13-enoic acid;
13E-9-oxo-11α,15S-dihydroxy-16R-methyl-18,19,20-trinor-17-(2'-furyl)-prosta-13-enoic acid,
the corresponding 15R epimers and 15RS mixtures, the $C_1$-$C_6$ alkyl esters and ethoxyethyl esters and the pharmaceutically or veterinarily acceptable salts of the free acids.

Particularly preferred specific compounds of the invention are:
5Z,13E-9-oxo-11α,15S-dihydroxy-16S-methyl-18,19,20-trinor-17-(2'-furyl)-prosta-5,13-dienoic acid;
5Z,13E-9-oxo-11α,15S-dihydroxy-16R-methyl-18,19,20-trinor-17-(2'-furyl)-prosta-5,13-dienoic acid;
13E-9-oxo-11α,15S-dihydroxy-16S-methyl-18,19,20-trinor-17-(2'-furyl)-prosta-13-enoic acid;
5Z,13E-9-oxo-11α,15S-dihydroxy-16S-methyl-18,19,20-trinor-17-(2'-furyl)-prosta-5,13-dienoic acid methyl ester;
5Z,13E-9-oxo-11α,15S-dihydroxy-16R-methyl-18,19,20-trinor-17-(2'-furyl)-prosta-5,13-dienoic acid methyl ester;
13E-9-oxo-11α,15S-dihydroxy-16S-methyl-18,19,20-trinor-17-(2'-furyl)-prosta-13-enoic acid methyl ester,
the corresponding 15R epimers and 15R,S mixtures, and the pharmaceutically or veterinarily acceptable salts of the free acids.

The compounds of formula (I) are prepared by a process comprising:
(a) submitting to reduction or Grignard reaction the $C_{15}$ carbonyl group of a compound of formula (II)

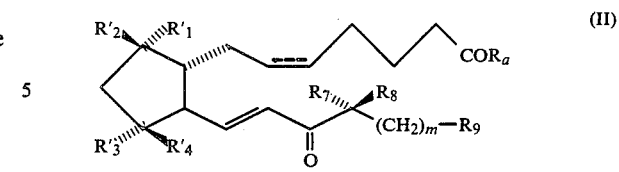

wherein
$R_7$, $R_8$, $R_9$ and m are as defined above; $R_a$ is the group R, as defined above, or a group —OQ wherein Q is a protecting group for the carboxylic function; one of $R_1'$ and $R_2'$ is hydrogen and the other is a free or protected hydroxy, or $R'_1$ and $R'_2$, taken together, form a protected oxo group; one of $R'_3$ and $R'_4$ is hydrogen and the other is a free or protected hydroxy; and
in any order, removing the protecting groups possibly present and, if desired, separating the obtained epimeric mixture of the 15R and 15S alcohols into the single epimers; or
(b) oxidizing a compound of formula (III)

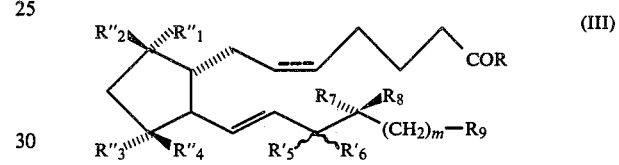

wherein
R, $R_7$, $R_8$, $R_9$ and m are as defined above; one of $R''_1$ and $R''_2$ is hydrogen and the other is free hydroxy; one of $R''_3$ and
$R''_4$ is hydrogen and the other is a protected hydroxy;
one of $R'_5$ and $R'_6$ is hydrogen,
$C_1$-$C_6$ alkyl, $C_2$-$C_6$ alkenyl, $C_2$-$C_6$ alkenyl or phenyl, and the other is a protected hydroxy, and removing the protecting groups, so obtaining a compound of formula (I) wherein $R_1$ and $R_2$, together, form an oxo group; or
(c) reacting a compound of formula (IV)

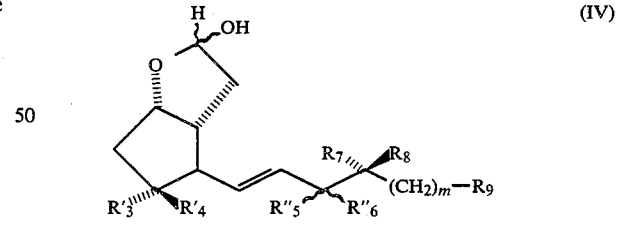

wherein
$R'_3$, $R'_4$, $R_7$, $R_8$, $R_9$ and m are as defined above; one of $R''_5$ and $R''_6$ is a free or protected hydroxy and the other is hydrogen, $C_1$-$C_6$ alkyl, $C_2$-$C_6$ alkenyl, $C_2$-$C_6$ alkynyl or phenyl, with a Wittig reagent comprising a group of formula —(CH$_2$)$_4$—COR wherein R is as defined above, and removing the protecting groups possibly present, so obtaining a compound of formula (I) wherein the symbol $\rightleftharpoons$ represents a cis double bond, $R_1$ is hydroxy and $R_2$ is hydrogen, and, if desired, converting the obtained compound into the corresponding compound of formula (I) wherein $R_1$ is hydrogen and $R_2$ is hydroxy, or into the corresponding compound of formula (I) where R₁ and R₂, taken together, form an oxo group;

and, if desired, converting a compound of formula (I) wherein R is —OH and wherein the hydroxy groups present may be free or protected, or a reactive derivative thereof, into a compound of formula (I) wherein R is other than —OH through esterification or amidation reactions followed by removal of the protecting groups possibly present, and/or, if desired, salifying a compound of formula (I) or obtaining a free compound of formula (I) from a salt thereof, and/or, if desired, separating a mixture of isomers of formula (I) into the single isomers. In the above formulae (II) to (IV) a protected hydroxy group is an etherified or esterified hydroxy group easily convertible to free hydroxy group under mild, either acidic or basic, conditions.

Examples of etherified hydroxy groups are silyl ethers: for instance tri-alkylsilyl ethers like trimethyl-, dimethyl-tert-butyl-, dimethyl-isopropyl-, or dimethylethylsilyl ether; and also acetal and enol ethers: for instance, tetrahydropyranyl ether, tetrahydrofuranyl ether, dioxanyl ether, oxathianyl ether, or one of the following

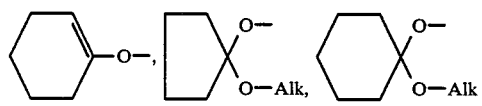

where Alk is C₁-C₆ alkyl.

Examples of esterified hydroxy groups are aliphatic or aromatic carboxylic $C_2$-$C_{10}$ acyloxy groups such as, e.g., acetoxy, benzoyloxy or substituted benzoyloxy, e.g. p-nitro-benzoyloxy or p-phenyl benzoyloxy.

A protected oxo group is an oxo group protected, e.g., as acetal, thioacetal, ketal or thioketal, in particular, for example, as dimethoxy acetal, dimethylthioacetal ethylenedioxyketal or ethylenedithioketal.

A protecting group (Q) for the carboxylic function may be any known carboxy protecting group easily removable under mild conditions, such as, for instance, tetrahydropyranyl or trimethylsilyl.

The reduction of the $C_{15}$ carbonyl group of a compound of formula (II) may be carried out by any reducing agent which is suitable for reducing ketones to alcohols in particular, for example, a boron or aluminium hydride complex such as, e.g., sodium boron hydride, lithium boron hydride, zinc boron hydride, tri-isobutyl boron hydride, tri-isobutyl potassium boron hydride, or a tri-$C_1$-$C_6$-alkoxy aluminium hydride, e.g. tri-tert-.butoxy-aluminium hydride.

Any suitable anhydrous or aqueous organic solvent may be used for the reduction, for instance diethyl ether, tetrahydrofuran, dioxane, dimethoxyethane, methanol or their mixtures; any temperature between about −40° C. and the boiling point of the solvent may be employed, preferred temperatures being between about −25° C. and about +25° C. The optional separation of the obtained mixture of the 15S and 15R epimeric secondary alcohols may be performed by fractional crystallization or by chromatography, for instance column cromatography, e.g. silica gel chromatography or HPLC preparative chromatography, or preparative TLC, using as eluant an appropriate mixture of solvents preferably chosen from the group consisting of methylene chloride, diethyl ether, ethyl acetate, n-hexane and cyclohexane.

The removal of the possibly present protecting groups, either on the mixture of the 15R and 15S alcohols, or on a separated 15R or 15S alcohol may be carried out in a conventional manner.

Thus, for example, the ether protecting groups may be removed from the hydroxyl functions with mild acid hydrolysis, for instance with mono- or poly-carboxylic acids like acetic, formic, citric, oxalic, or tartaric in a solvent like water, acetone, tetrahydrofuran, dimethoxyethane, or a low molecular weight alcohol, or with a sulfonic acid like p-toluene-sulfonic in a low molecular weight alcohol like anhydrous ethanol or methanol, or with a polystyrene-sulfonic resin.

For example, a 0.1–0.25N polycarboxylic acid (like oxalic or citric) is used with a suitable low-boiling solvent miscible with water and readily removable under vacuum at the end of the reaction.

Silyl ether residues may also be removed with F⁻ ions in solvents like tetrahydrofuran and dimethylformamide. Ester protecting groups, including carboxy protecting groups, may be, e.g., removed by following known saponification procedures, generally under mild basic conditions. When the removal of ester protecting groups of hydroxy functions is carried out on a compound containing an esterified carboxy group, the latter may also be simultaneously de-esterified.

Ketal and thioketal protecting groups are generally removed by mild acid hydrolysis as described above.

The Grignard reaction on the $C_{15}$ carbonyl group of a compound of formula (II) may be carried out reacting the compound of formula (II) with a Grignard reagent of formula $R_8MgY$ wherein $R_8$ is $C_1$-$C_6$ alkyl, $C_2$-$C_6$ alkenyl, $C_2$-$C_6$ alkynyl or phenyl and Y is chlorine, bromine or iodine.

The reaction is preferably performed in an anhydrous solvent, such as, for instance, diethyl ether, tetrahydrofuran, dioxane, dimethylsulphoxide, benzene or toluene, at a temperature which may vary from about −70° C. to the boiling point of the solvent, preferred temperatures being from about −60° C. to about +20° C.

The initially formed organometallic complex may be decomposed by hydrolysis using, e.g., saturated aqueous ammonium chloride according to conventional procedures. The optional separation of the obtained mixture of the 15S and 15R epimeric tertiary alcohols, and the removal of the protecting groups possibly present may be performed as indicated hereabove with regard to the reduction of the compound of formula (II).

The oxidation of a compound of formula (III) may be carried out by means of oxidizing agents such as, for example, $CrO_3$ or the Jones reagent (G. I. Poos and al., J. Am. Chem. Soc. 75, 422, 1953) or the Moffatt reagent (J. Am. Chem. Soc. 87, 5661, 1965), operating in a suitable solvent which may be, for example, acetone, dioxane, benzene or dimethylsulphoxide at a temperature which may vary from the room temperature to the boiling point of the used solvent. For the oxidation the procedure described in Tetr. Lett. 2235, 1974, may also be followed.

Again the subsequent removal of the protecting groups may be performed as reported before. The Wittig reagent used for the reaction with a compound of formula (IV) may be a compound of formula

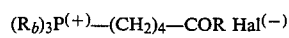

wherein R is as defined above, Hal is bromine or chlorine and $R_b$ is $C_1$-$C_6$ alkyl or phenyl.

The preparation of the Wittig reagent is discussed in detail by Tripett, Quart. Rev., 1963, XVII, No. 4, 406.

The reaction between a compound of formula (IV) and the Wittig reagent may be performed using a slight excess of the Wittig reagent per mole of lactol (IV), operating in an inert organic solvent such as, e.g., diethyl ether, tetrahydrofuran, n-hexane, dimethylsulphoxide, dimethylformamide or hexamethylphosphoramide, in the presence of a base which may be, for instance, sodium hydride or potassium tert.butoxide.

The temperature may vary between about 0° C. and the reflux temperature of the reaction mixture, although the reaction is preferably performed at room temperature or below.

The subsequent removal of the protecting groups possibly present may be carried out as previously indicated. The optional conversion of an obtained compound of formula (I) wherein $R_1$ is hydroxy and $R_2$ is hydrogen into one wherein $R_1$ is hydrogen and $R_2$ is hydroxy may be performed following the procedures described, e.g., in U.K. patent specification No. 1498105, while the optional conversion of the same compound into one wherein $R_1$ and $R_2$, taken together, form an oxo group, may be carried out using analogous conditions as those previously reported for the oxidation of a compound of formula (III). A reactive derivative of a compound of formula (I) wherein R is OH may be, for example, an ester thereof, e.g. a $C_1$-$C_6$ alkyl ester, or an acyl halide, e.g. the chloride, or the anhydride or a mixed anhydride thereof.

The optional conversion of a compound of formula (I) wherein R is OH, or a reactive derivative thereof, into a corresponding compound wherein R is other than OH through esterification and amidation reactions may be performed according to conventional methods.

For example, a compound of formula (I) wherein R is OH may be converted into a compound of formula (I) wherein R is —OR′, where R′ is as defined above, by the known procedures reported in the organic chemistry for the esterification of a carboxylic acid. The carboxylic acid or a reactive derivative thereof such as, for instance, an acyl halide, e.g. the chloride, or the anhydride or a mixed anhydride, or the corresponding azide may be, e.g., reacted with an alcohol of formula R′OH, where R′ is as defined above, operating either at room temperature or under cooling in a suitable solvent such as, e.g., dioxane, tetrahydrofuran, benzene, toluene, chloroform, methylene chloride, dimethylformamide, and, if necessary, according to the starting material used, either in the presence of a condensing agent such as, for instance, a carbodiimide, e.g. dicyclohexylcarbodiimide, carbonyldiimidazole and the like, or in the presence of a base which may be, for instance, sodium bicarbonate or carbonate, potassium carbonate or bicarbonate, an organic amine, e.g. triethylamine, or another acid acceptor such as, e.g., an anionic exchange resin.

In analogous fashion a compound of formula (I) wherein R is OH may be converted into a compound of formula (I) wherein R is —W—$(CH_2)_n$—X wherein W, n and X are as defined above. In particular, for example, this conversion may be carried out reacting a compound of formula (I) where R is OH with a compound of formula H—W—$(CH_2)_n$—X in the presence of a dehydrating agent, e.g. one of those hereabove indicated, operating in an inert solvent such as, e.g. chloroform, methylene chloride, diethyl ether, tetrahydrofuran, dimethylformamide, benzene, toluene, n-pentane, n-hexane and the like and, if desired, in the presence of a suitable acylation catalyst, e.g. pyridine or 4-dimethylamino pyridine (DMAP). The reaction is conveniently made in two steps wherein the first step is the preparation of the substituted isourea derivative of formula (V)

(V)

wherein W, n and X are as defined above and each of $R_c$ and $R_d$ is, independently, an optionally substituted $C_1$-$C_6$ alkyl radical, e.g. ethyl, isopropyl, 3-dimethylaminopropyl, or a cycloalkyl radical, e.g. cyclohexyl; and wherein the second step is the reaction of this compound with the compound of formula (I).

The conversion of a compound of formula (I) wherein R is OH into a compound of formula (I) wherein R is OR′, wherein R′ is $C_1$-$C_6$ alkyl may also be performed through reaction with the appropriate diazo-$C_1$-$C_6$ alkane, e.g. diazomethane, diazoethane and the like, preferably operating at room temperature or under cooling, in an anhydrous organic solvent chosen, e.g., from the group of diethyl ether, tetrahydrofuran or dioxane.

The conversion of a compound of formula (I) wherein R is OH into a compound of formula (I) wherein R is

wherein R″ and R‴ are as defined above, may be carried out reacting a reactive derivative of the compound of formula (I), e.g. a $C_1$-$C_6$ alkyl ester thereof, e.g. the methyl or ethyl ester, or an acyl halide, e.g. the chloride, with the appropriate amine of formula

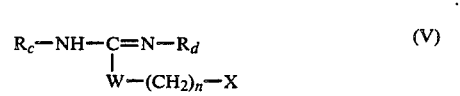

The reaction may be, for instance, carried out in an inert solvent such as, e.g. benzene, toluene, methanol, ethanol, diethyl ether, tetrahydrofuran or dimethylformamide, at any suitable temperature between the room temperature and the boiling point of the solvent.

When an acyl halide, e.g. the chloride, of a compound of formula (I) where R is OH is used for the reaction with the amine, then the presence of a base preferably an inorganic base such as, e.g., sodium carbonate or bicarbonate, is required and preferred solvents are, in this case, benzene or toluene.

In particular, a compound of formula (I) where R is

wherein R″ and R‴ are both hydrogen may be obtained from a $C_1$-$C_6$ alkyl ester, e.g. the methyl or ethyl ester, of a compound of formula (I) where R is OH, reacting the ester with gaseous ammonia in a lower aliphatic alcohol in a conventional manner.

The optional salification of a compound of formula (I) and the preparation of a free compound of formula (I) from a salt thereof may be carried out by standard procedures.

Also the optional separation of a mixture of isomers of formula (I) into the single isomers may be performed in a conventional manner e.g. by fractional crystallization or by chromatography as previously reported in this specification.

The compounds of formula (II) may be obtained reacting a compound of formula (VI)

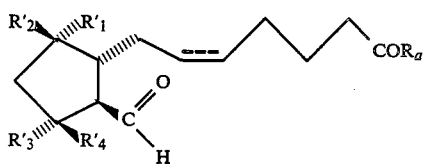
(VI)

wherein $R_a$, $R'_1$, $R'_2$, $R'_3$ and $R'_4$ are as defined above, with a compound of formula (VII)

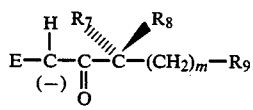
(VII)

wherein m, $R_7$, $R_8$ and $R_9$ are as defined above, and E is a group $(C_6H_5)_3$

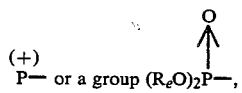

wherein each $R_e$ is, independently, $C_1$-$C_6$ alkyl or phenyl,
and, if desired, removing the protecting groups possibly present in the obtained compound. A compound of formula (III), may be obtained etherifying a compound of formula (VIII)

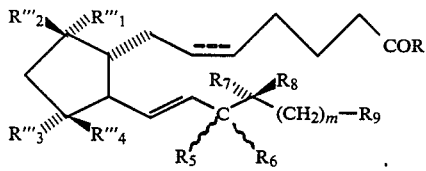
(VIII)

wherein R, m, $R_5$, $R_6$, $R_7$, $R_8$ and $R_9$ are as defined above, one of $R_1'''$, and $R_2'''$ is hydrogen and the other is as esterified hydroxy group, e.g. a $C_2$-$C_{10}$ carboxylic acyloxy group as defined above, in particular acetoxy, benzoyloxy, p-nitro-benzoyloxy or p-phenyl-benzoyloxy; one of $R_3'''$ and $R_4'''$ is hydrogen and the other is a free or etherified hydroxy, e.g. a silyloxy group or tetrahydropyranyloxy group, so obtaining a compound of formula (IX)

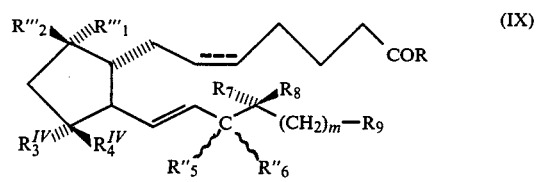
(IX)

wherein
R, $R_1''''$, $R_2''''$, $R_7$, $R_8$, $R_9$ and m are as defined above,
one of $R_3^{IV}$ and $R_4^{IV}$ is hydrogen and the other is an etherified hydroxy, e.g. a silyloxy or tetrahydropyranyloxy group, and
one of $R_5''$ and $R_6''$ is an etherified hydroxy, e.g. a silyloxy or tetrahydropyranyloxy group, and the other is hydrogen, $C_1$-$C_6$ alkyl, $C_2$-$C_6$ alkenyl; $C_2$-$C_6$ alkynyl or phenyl, and then de-esterifying, e.g. de-acylating, at the $C_9$ position the obtained compound of formula (IX).

The above mentioned etherification process may be carried out in a known manner, e.g. through reaction with a chlorosilane in the presence of a base, for instance imidazole or a trialkylamine, e.g. triethylamine, in order to obtain a silyl ether, or through reaction with dihydropyran in the presence of catalytic amount of, e.g., p-toluene-sulfonic acid, in order to obtain a tetrahydropyranyl ether.

The above said de-esterification, e.g. de-acylation, process, may be performed in a known manner too, generally operating under mild basic conditions, for example by reaction with an alkali metal hydroxide, e.g. sodium hydroxide, in an aqueous-alcoholic medium; or by transesterification in an appropriate dry alcohol, in the presence of a basic catalyst such as, e.g. an alkali metal carbonate, e.g. sodium carbonate, under nitrogen atmosphere at room temperature.

A compound of formula (IV) may be prepared reducing a compound of formula (X)

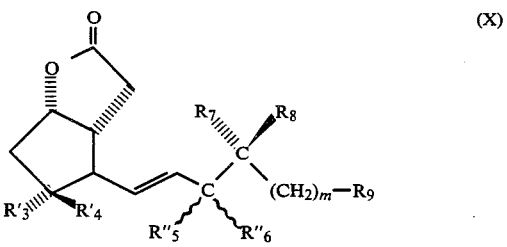
(X)

wherein $R'_3$, $R'_4$, $R''_5$, $R''_6$, $R_7$, $R_8$, $R_9$ and m are as defined above. The reduction may be, e.g., performed by treatment with diisobutyl aluminium hydride or sodium bis-(2-methoxy-ethoxy)-aluminium hydride in an inert solvent, for example, toluene, n-heptane, n-hexane or benzene or their mixtures, at below 30° C.

The compounds of formula (VI) are known compounds [T. S. Bindra and R. Bindra, Prostaglandin Synthesis, Acad. Press, New York, 1977, 236], or may be prepared by known methods from known compounds.

A carbanion compound of formula (VII) may be prepared by treatment of a compound of formula (XI)

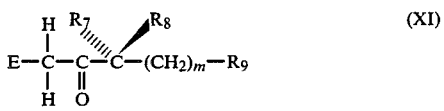

wherein E, $R_7$, $R_8$, $R_9$ and m are as defined above, with an equivalent amount of a base which is preferably selected from sodium hydride, lithium hydride, calcium hydride, a $C_1$–$C_6$ alkyl, e.g. methyl, lithium derivative, or an alkali metal, e.g. sodium, methylsulfonyl methide. The compounds of formula (XI) are known compounds or may be obtained by known methods following reaction conditions well known to the skilled in the art starting, e.g., from an α-substituted carboxy compound of formula (XII)

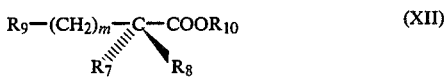

wherein $R_{10}$ is a branched or straight chain $C_1$–$C_6$ alkyl group.

The compounds of formula (XII) may be prepared by known methods from known compounds, either in racemic or optically active form, e.g. as described by P. Lambert in Rev. Nickel 21, 79 (1955) and by L. A. Yanovskaya et al. in Tetr. 23, 1311 (1967).

For instance, an optically active compound of formula (XII) wherein $R_7$ is methyl, $R_8$ is hydrogen, m is 1 and $R_9$ is unsubstituted 2-furyl may be prepared reacting a compound of formula (XIII)

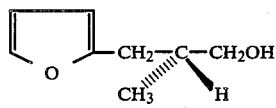

[in its turn obtained in optically pure form in the yeast fermentation of known α-methyl-β-(2-furyl)-acrolein (C. Fuganti and P. Grasselli, J. Chem. Soc. Chem. Comm. 205, 1982)] in a two steps oxidation process, firstly with Pfitzner Moffatt reagent (K. E. Pfitzner and J. G. Moffatt, J. Am. Chem. Soc. 87, 5661, 1965), and, secondly, with $Ag_2O$ in THF aqueous solution in analogy with the methods of Campaigne and Pearl (E. Campaigne, W. M. Le Suer, Org. Synt. Coll. 4, 919, 1963; I. A. Pearl ibid, 4, 972, 1963), and subsequently esterifying the obtained carboxylic acid.

The compound having the formula (VIII) may be prepared following procedures which are usual in the prostaglandin chemistry, for instance through esterification and etherification reactions carried out on a corresponding formula (I) compound, or through reaction between an aldehyde corresponding to one of formula (VI), wherein, however, $R'_1$, $R'_2$, $R'_3$ and $R'_4$ have the meanings given for the corresponding substituents in the formula (VIII), and a compound of formula (VII).

The compound of formula (VIII) may be prepared too following procedures well known in the prostaglandin chemistry, for example those described in U.K. patent specification No. 1493557 for the synthesis of analogous compounds.

The compounds of formula (I) may be used on mammals in all the conditions where natural prostaglandins are indicated, and administered by the usual routes, e.g. orally, parenterally, rectally, intravaginally, or by aerosol, with the advantages of a superior resistence to enzyme-induced metabolic degradation, for instance with respect to the enzyme 15-prostaglandin dehydrogenase which, as is known, rapidly inactivates natural prostaglandins.

The compounds of formula (I) are also endowed with longer lasting therapeutic activity than natural prostaglandins, when administered by usual routes and especially when administered by oral route.

Furthermore the protaglandins of formula (I) are more potent in biological responses and have a narrower spectrum of biological potency than the known prostaglandins, showing more specificity in their activity and causing smaller and fewer undesired side-effects.

Thus, for example, the compounds of formula (I) wherein $R_1$ and $R_3$ are hydroxy are provided with an outstanding luteolytic activity: the compound of the invention 5Z,13E-9α,11α,15S-trihydroxy-16S-methyl-18,19,20-trinor-17-(2'-furyl)-prosta-5,13-dienoic acid methyl ester, for instance, was found to be 10–20 times more potent than natural $PGF_{2α}$ in hamster luteolytic activity, while the corresponding 16-unsubstituted derivative, 5Z,13E,9α,11α,15S-trihydroxy-18,19,20-trinor-17-(2'-furyl)-prosta-5,13-dienoic acid methyl ester was found to be only equipotent as $PGF_{2α}$.

The luteolytic activity in hamster was evaluated according to the procedure reported by A. B. Labhstwar in Nature 230, 528, 1971.

Furthermore the compounds of formula (I), in particular those wherein $R_1$ and $R_2$, taken together, form an oxo group, and $R_3$ is hydroxy, are endowed with remarkable abortive activity as is shown in the following table I reporting the comparison between the compound of the invention 5Z,13E-9-oxo-11α,15S-dihydroxy-16S-methyl-18,19,20-trinor-17-(2'-furyl)-prosta-5,13-dienoic acid methyl ester (compound A) and the reference compound 5Z,13E-9-oxo-11α,15S-dihydroxy-18,19,20-trinor-17-(2'-furyl)-prosta-5,13-dienoic acid methyl ester (compound B).

TABLE I

| Structure | Guinea Pig abortion $ED_{50}$ μg/kg s.c. |
|---|---|
| (A) 5Z,13E-9-oxo-11α,15S-dihydroxy-16S-methyl-18,19,20-trinor-17-(2'-furyl)-prosta-5,13-dienoic acid methyl ester | 2 |
| (B) 5Z,13E-9-oxo-11α,15S-dihydroxy-18,19,20-trinor-17-(2'-furyl)-prosta-5,13-dienoic acid methyl ester | >30 |

The abortion data reported in table (I) were obtained according to the procedure reported by W. Elger in Animal Reproduction Science vol. 2, 133, 1979. High abortive activity is displayed also by the analogous compounds of the $PGE_1$ series, i.e. compounds of formula (I) wherein the symbol ==== represents a single bond; for instance, when the compound 13E-9-oxo-11α,15S-dihydroxy-16S-methyl-18,19,20-trinor-17-(2'-furyl)-prosta-13-enoic acid methyl ester was tested for abortion in Guinea pig by the same above indicated procedure, an effective dose ED$_{50}$ value of 0.5 μg/kg s.c. was found.

The above reported results indicate that the presence of an alkyl substituent at the C$_{16}$ chiral center, characterizing specifically the compounds of the invention, leads to an improvement of both the luteolytic and the abortifacient activity.

For the use as luteolytic or abortifacient agents the compounds of formula (I) may be, e.g., administered orally, parenterally or by intravenous or intrauterine way, the parenteral, intravenous and intrauterine routes being the preferred ones.

For instance they can be administered by intravenous infusion of a sterile isotonic saline solution at a dose of about 0.001 to 5, preferably 0.005 to 1, μg/kg of mammal body weight per minute, the exact dose depending on the conditions of the patient to be treated.

Another useful pharmacological property of the compounds of formula (I), particularly the 9-oxo derivatives, is their anti-ulcerogenic activity, as is proved by the fact that they have been found to be active in preventing ethanol induced, stress-induced or ASA-induced gastric ulcers and indomethacin induced intestinal ulcers [Gastroenter. 77, 761-767, 1980; Prostaglandins and Medicine vol. 5, 131-139, 1980], and in inhibiting gastric secretion according to the method of Shay et al. [Gastroenter. 26, 906, 1954].

In particular the compounds of the invention are able to prevent formation of ulcerogenic gastric lesions and, differently from PGE$_2$, taken as the standard compound, are devoided of stimulating effect on the smooth muscles such as, e.g., the ileum of guinea-pigs.

Thus, for example the same compounds (A) and (B) indicated in table I were compared with the activity of the PGE$_2$ taken as standard, as regards the inhibition of the ethanol and indomethacin induced gastric ulcers and also as regards the guinea pig ileum contracting activity.

The obtained results, reported in the following table (II) show that a remarkable increase of the cytoprotective and anti-ulcer activity is achieved with the compound (A) of the invention while a reduced stimulating activity on ileum is maintained both with respect to the PGE$_2$ standard and with respect to the 16 unsubstituted reference compound (B), indicating a low incidence of the undesired side-effects.

TABLE II

| | In vivo Inhibition of gastric ulcers in rats (os) - potency ratio | | In vitro Guinea pig ileum contracting activity - potency ratio |
|---|---|---|---|
| | Ethanol | Indomethacin | |
| PGE$_2$ | 1 | 1 | 1 |
| (A) | 79 | 12 | 0.04 |
| (B) | 1.3 | 0.16 | 0.07 |

As already said, the inhibition of the ethanol induced gastric ulcers in rats was evaluated in accordance with the procedure described in Gastroenter. 77, 761-767, 1950, and the inhibition of the indomethacin induced gastric ulcers in rats was evaluated according to the procedure described in Prostaglandins and Medicine 5, 131-139, 1980.

The guinea pig ileum contracting activity was determined according to the following procedure: ileum segments obtained from male Guinea pig were placed under 0.5 g tension in a 10 ml thermostatic bath held at 35° C., containing Tyrode ® solution gassed with a mixture of O$_2$ and CO$_2$. The tissue was left 30 minutes to stabilize before the compounds were tested. The response was recorded using an isotonic transducer. Log-dose response curves of the tested compounds were compared.

In view of this activity the compounds of formula (I) are useful to reduce and control excessive gastric secretion in mammals and therefore to reduce or eliminate the formation of gastrointestinal ulcers and, at the same time, they are able to accelerate the healing process of any ulcers already present in the gastrointestinal tract. The compounds of formula (I) are consequently also useful for reducing the undesirable gastrointestinal side-effects resulting from systemic administration of anti-inflammatory prostaglandin synthetase inhibitors and may be, therefore, used for this purpose in association with them. The compounds of formula (I) in accordance with these purposes can be, e.g., administered orally, parenterally, e.g. by intravenous injection or infusion, or by intramuscular injection, by inhalation or rectally, the oral route being particularly preferred. When administered orally, the compounds of the invention may be used at a dosage ranging from about 1 mg to about 10 mg, preferably 5 mg, once or three times a day. In intravenous infusion, the dosage varies from approximately 0.01 μg to 0.05 μg per kilogram of body weight per minute. The total daily dose, both by injection and by infusion, may vary from about 0.1 to about 20 mg. Of course, in the treatment of the above conditions, the exact treatment level depends on the case history of the patient to be treated. The compounds of formula (I), in particular the 9-oxo derivatives, compete with natural PGE$_1$ and PGI$_2$ with regard to the hypotensive and vasodilatory activity and blood platelet antiaggregating and disaggregating properties. In particular, for instance, they were found to inhibit at low dosages the platelet aggregation induced in vitro by 0.4 μg/ml ADP in guinea-pig platelet rich plasma: in this test, for example, the compound 13E-9-oxo-11α,15S-dihydroxy-16S-methyl-18,19,20-trinor-17-(2'-furyl)-prosta-13-enoic acid was six times more potent then natural PGE$_1$. In view of the above indicated activities the compounds of the invention can be used as hypotensive and vasodilatory agents and, particularly, for inhibiting platelet aggregation, decreasing adhesion, preventing clot formation and dissolving thrombi and, more generally, for treating conditions of hyperlipidaemia such as, for instance, atherosclerosis and arteriosclerosis. The compounds of formula (I), particularly the 9-oxo-derivatives, are also useful antineoplastic agents, as is proved, e.g., by the fact that they were found to be active in inhibiting B-16 melanoma growth in vitro and in vivo tests. Thus, for example, in vivo experiments carried out on mice intraperitoneally treated for 4 consecutive days with the compounds of the invention at daily doses varying from 0.25 to 5 mg/kg, according to Hofer et al. J. Surg. Res. 32, 552, 1982, showed an evident and significant inhibition of the tumor growth.

The toxicity of the compounds of the invention was found to be quite negligible and therefore they can be safely used in therapy.

The pharmaceutical compositions of the invention are usually prepared following conventional methods and are administered in a pharmaceutically suitable form. For example, the solid oral forms may contain, together with the active compound, diluents, e.g., lactose, dextrose, saccharose, cellulose, corn starch and potato starch; lubricants, e.g. silica, talc, stearic acid, magnesium or calcium stearage, and/or polyethylene glycols; binding agents, e.g. starches, arabic gums, gelatin, methylcellulose, carboxymethyl cellulose, polyvinyl pyrrolidone; disaggregating agents, e.g. a starch, alginic acid, alginates, sodium starch glycolate; effervescing mixtures; dyestuffs; sweeteners; wetting agents, for instance, lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes. The liquid dispersions for oral administration may be, e.g., syrups, emulsions and suspensions.

The syrups may contain as carrier, for example, saccharose or saccharose with glycerine and/or mannitol and/or sorbitol; in particular a syrup to be administered to diabetic patients can contain as carriers only products not metabolizable to glucose, or metabolizable in very small amount to glucose such as, sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

The solutions for intravenous injections or infusions may contain as carrier, for example, sterile water or, preferably, they may be in the form of sterile aqueous isotonic saline solutions.

The suppositories and the vaginal tablets may contain, together with the active compound, a pharmaceutically acceptable carrier, e.g. cocoa-butter, polyethylene glycol, a polyoxyethylene sorbitan fatty acid ester surfactant or lecithin.

The compositions may also comprise a suspension or a solution of the active ingredient in a conventional liquefied propellant, such as dichlorodifluoromethane or dichlorotetrafluoroethane, to be administered from a pressurized container, i.e., an aerosol dispenser. When the medicament is not soluble in the propellant, it may be necessary to add a co-solvent, such as, ethanol, dipropylene glycol, isopropyl myristate, and/or a surface-active agent to the propellant medium and such surface-active agent may be any of those commonly used for this purpose, such as nonionic surface-active agents, e.g., lecithin. Other suitable pharmaceutical forms may be for example powders.

The powders may be administered by means of a suitable insufflator device and in this case the fine particle sized powders of the active ingredient may be mixed with a diluent material such as lactose.

This invention is illustrated but not limited by the following examples wherein the abbreviation DHP, THF, THP, DMSO, DIBA, DCC and HPLC stand, respectively, for diidropyran, tetrahydrofuran, tetrahydropyran, dimethylsulphoxide, diisobutylaluminium hydride, dicyclohexylcarbodiimide and high pressure liquid chromatography.

EXAMPLE 1

Under a dry argon atmosphere, a solution of 0.378 g of dimethyl{[2-oxo-3S-3-methyl-4-(5-methyl-2-furyl)]-butyl}phosphonate in 5 ml of dry benzene was added dropwise to a stirred slurry of 0.044 g of 80% N$_a$H (dispersion in mineral oil) in 5 ml of dry benzene, with exclusion of moisture. Stirring was continued until the evolution of hydrogen had stopped; then a solution of 1α-[7'-(methoxy-carbonyl)-hex-5'(Z)-enyl]-2β-formyl-3α-hydroxy-5α-acetoxy-cyclopentane (0.510 g) in dry benzene (5 ml) was added at once.

The mixture was stirred for 1 hour at 25° C., then neutralized with acetic acid, and stirring was continued for 30 minutes. The organic phase was washed until neutral with water, dried, and the solvent was removed by evaporation in vacuum.

The crude product was purified by chromatography, using diethyl ether: ethyl alcohol mixture (95:5) as eluant, to give 0.51 g of pure 5Z,13E-9α,11α-dihydroxy-15-oxo-16S-methyl-18,19,20-trinor-17-(5'-methyl-2'-furyl)-prosta-5,13-dienoic acid methyl ester, 9-acetate, [α]$_D$=+36.2° (C=1, CHCl$_3$).

Using the same procedure, starting from the saturated 1α-[7'-(methoxy-carbonyl)-hexyl]-2β-formyl-3α-hydroxy-5α-acetoxy-cyclopentane, the corresponding 13E-9α,11α-dihydroxy-15-oxo-16S-methyl-18,19,20-trinor-17-(5'-methyl-2'-furyl)-prosta-13-enoic acid methyl ester-9-acetate was obtained, and starting from 1α-[7'-(methoxy-carbonyl)-hex-5'(Z)-enyl]-2β-formyl-5α-acetoxy-cyclopentane, and 1α-[7'-(metoxy-carbonyl)-hexyl]-2β-formyl-5α-acetoxy-cyclopentane, 5Z,13E-9α-hydroxy-15-oxo-16S-methyl-18,19,20-trinor-17-(5'-methyl-2'-furyl)-prosta-5,13-dienoic acid methyl ester-9-acetate, and 13E-9α-hydroxy-15-oxo-16S-methyl-18,19,20-trinor-17-(5'-methyl-2'-furyl)-prosta-13-enoic acid methyl ester, 9-acetate were prepared, respectively.

EXAMPLE 2

A solution of 5Z,13E-9α,11α-dihydroxy-15-oxo-16S-methyl-18,19,20-trinor-17-(5'-methyl-2'-furyl)-prosta-5,13-dienoic acid methyl ester, 9-acetate (1.26 g) in methanol (25 ml) was dropped into a stirred solution of N$_a$BH$_4$ (0.315 g) in methanol (30 ml) cooled to −30° C. with external cooling bath.

The temperature was maintained between −25° C. and −30° C. for 20 minutes after the addition was completed.

The solution was then neutralized with acetic acid and the mixture was left to rise to room temperature. The solution was diluted with 50 ml of ethyl acetate and washed with brine, dried, and the solvent was removed by evaporation. The crude epimeric mixture of 5Z,13E-9α-11α,15(RS)-trihydroxy-16S-methyl-18,19,20-trinor-17-(5'-methyl-2'-furyl)-prosta-5,13-dienoic acid methyl ester, 9-acetate was separated into the two 15S and 15R epimers by chromatographic purification on silica gel using ethyl acetate: n-hexane (9:1) as eluant to give 0.49 g of 5Z,13E-9α,11α,15S-trihydroxy-16S-methyl-18,19,20-trinor-17-(5'-methyl-2'-furyl)-prosta-5,13-dienoic acid methyl ester, 9-acetate, $[α]_D = +32.7°$ (C=1, CHCl$_3$), and 0.51 g of the corresponding 15R epimer 5Z,13E-9α,11α,15R-trihydroxy-16S-methyl-18,19,20-trinor-17-(5'-methyl-2'-furyl)-prosta-5,13-dienoic acid methyl ester, 9-acetate, $[α]_D = +9.8°$ (C=1, CHCl$_3$).

EXAMPLE 3

A stirred solution of 0.25 g of 5Z,13E-9α,11α,15S-trihydroxy-16S-methyl-18,19,20-trinor-17-(5'-methyl-2'-furyl)-prosta-5,13-dienoic acid methyl ester, 9-acetate in methanol (10 ml) was treated with a solution of 0.10 g of lithium hydroxyde in water (1 ml).

The mixture was stirred at room temperature for 6 hours then neutralized to pH 6.2 with 10% N$_a$H$_2$PO$_4$ aqueous solution, extracted with ethyl acetate, washed with brine and dried; the solvent was removed to obtain 0.22 g of 5Z,13E-9α,11α,15S-trihydroxy-16S-methyl-18,19,20-trinor-17-(5'-methyl-2'-furyl)-prosta-5,13-dienoic acid, $[α]_D = +26.8°$ (C=1, ethanol).

According to the above described procedure, starting from 5Z,13E-9α,11α,15R-trihydroxy-16S-methyl-18,19,20-trinor-17-(5'-methyl-2'-furyl)-prosta-5,13-dienoic acid methyl ester, 9-acetate, pure 5Z,13E-9α,11α,15R-trihydroxy-16S-methyl-18,19,20-trinor-17-(5'-methyl-2'-furyl)-prosta-5,13-dienoic acid was obtained, $[α]_D = +5.5°$ (C=1, ethanol).

By analogous procedure the following compounds were prepared, wherein the $[α]_D$ values are for C=1 concentrations in ethanol:

5Z,13E-9α,11α,15S-trihydroxy-16S-methyl-18,19,20-trinor-17-(2'-furyl)-prosta-5,13-dienoic acid, $[α]_D = +28.2°$;

5Z,13E-9α,11α,15S-trihydroxy-16S-methyl-18,19,20-trinor-17-(3'-furyl)-prosta-5,13-dienoic acid, $[α]_D = +27.5°$;

5Z,13E-9α,11α,15S-trihydroxy-16S-ethyl-18,19,20-trinor-17-(2'-furyl)-prosta-5,13-dienoic acid, $[α]_D = +29°$;

5Z,13E-9α,11α,15S-trihydroxy-16S-ethyl-18,19,20-trinor-17-(3'-furyl)-prosta-5,13-dienoic acid, $[α]_D = +24.8°$;

5Z,13E-9α,11α,15S-trihydroxy-16S-ethyl-18,19,20-trinor-17-(5'-methyl-2'-furyl)-prosta-5,13-dienoic acid, $[α]_D = +27°$;

5Z,13E-9α,11α,15S-trihydroxy-16S-methyl-18,19,20-trinor-17-(5'-ethyl-2'-furyl)-prosta-5,13-dienoic acid, $[α]_D = +31.6°$; and the corresponding 16R-epimers, in particular:

5Z,13E-9α,11α,15S-trihydroxy-16R-methyl-18,19,20-trinor-17-(2'-furyl)-prosta-5,13-dienoic acid, $[α]_D = +30.6°$;

5Z,13E-9α,11α,15S-trihydroxy-16R-methyl-18,19,20-trinor-17-(3'-furyl)-prosta-5,13-dienoic acid, $[α]_D = +31°$, and the 15R-epimers of all the above indicated compounds.

EXAMPLE 4

A 0.1N solution of CH$_3$M$_g$J in diethyl ether was dropped into a solution of 5Z,13E-9α,11α-dihydroxy-15-oxo-16S-methyl-18,19,20-trinor-17-(2'-furyl)-prosta-5,13-dienoic acid-1-trimethylsilyl ester-9,11-bis-trimethylsilyl ether (0.86 g.) in 15 ml of dry diethyl ether.

The reaction mixture was stirred for 1 hour, treated with aqueous acetic acid, then washed with saturated (NH$_4$)Cl aqueous solution, extracted with diethyl ether, washed with water and the organic phase was finally dried and evaporated to dryness.

The crude mixture of the 15-epimeric alcohols was separated by silica gel coluum using methylene chloride: ethanol (90:10) as eluant to give 0.28 g of pure 5Z,13E-9α,11α,15S-trihydroxy-15,16S-dimethyl-18,19,20-trinor-17-(2'-furyl)-prosta-5,13-dienoic acid, [mass spectrum (tetra-trimethylsilyl derivative): M/e 694, 605, 516, 427] and 0.21 g of pure 5Z,13E-9α,11α,15R-trihydroxy-15,16S-dimethyl-18,19,20-trinor-17-(2'-furyl)-prosta-5,13-dienoic acid, [mass spectrum (tetra-trimethylsilyl derivative): M/e 694, 605, 516, 427; NMR (CDCl$_3$) δppm: 1.00 (3H, d; CH$_3$—C$_{17}$); 4.43 (2H, m; Δ5,6); 5.58 (2H, m; Δ13,14); 6.01; 6.27, 7.28 (3H; furyl)].

Using the same procedure the following compounds were prepared:

5Z,13E-9α,11α,15S-trihydroxy-15,16S-dimethyl-18,19,10-trinor-17-(2'-furyl)-prosta-5,13-dienoic acid;

5Z,13E-9α,11α,15S-trihydroxy-15,16S-dimethyl-18,19,20-trinor-17-(3'-furyl)-prosta-5,13-dienoic acid;

5Z,13E-9α,11α,15S-trihydroxy-15-methyl-16S-ethyl-18,19,20-trinor-17-(2'-furyl)-prosta-5,13-dienoic acid;

5Z,13E-9α,11α,15S-trihydroxy-15-methyl-16S-ethyl-18,19,20-trinor-17-(3'-furyl)-prosta-5,13-dienoic acid;

5Z,13E-9α,11α,15S-trihydroxy-15-16S-dimethyl-18,19,20-trinor-17-(5'-methyl-2'-furyl)-prosta-5,13-dienoic acid;

5Z,13E-9α,11α,15S-trihydroxy-15-methyl-16S-ethyl-18,19,20-trinor-17-(5'-methyl-2'-furyl)-prosta-5,13-dienoic acid;

5Z,13E-9α,11α,15S-trihydroxy-15-16S-dimethyl-18,19,20-trinor-17-(5'-ethyl-2'-furyl)-prosta-5,13-dienoic acid; and the corresponding 15R and 16R-epimers.

EXAMPLE 5

To a solution of 0.260 g of 5Z,13E-9α,11α,15S-trihydroxy-16S-methyl-18,19,20-trinor-17-(5'-methyl-2'-furyl)-prosta-5,13-dienoic acid, methyl ester, 9-acetate in 8 ml of dry CH$_2$Cl$_2$, 0.126 ml of DHP and 0.010 g of p-toluene-sulfonic acid were added.

The solution was stirred at room temperature (25° C.) for 2 hours, then it was diluted with 50 ml of diethyl ether and washed twice with 5% N HCO$_3$ aqueous solution, twice with water, and then dried.

The solvent was removed in vacuum, the crude was dissolved in 10 ml of methanol and 0.1 g of K$_2$CO$_3$ were added. The solution was stirred at room temperature for 6 hours then was treated with 30% aqueous solution of NaH$_2$PO$_4$ (35 ml) and extracted with 4 portions of 20 ml of ethyl acetate.

The organic phase was washed, dried, and the solvent was distilled in vacuum. The residue was purified by chromatography on silica gel with ethyl acetate: n-hexane (40:60) as eluant so obtaining 0.265 g of pure 5Z,13E-9α,11α,15S-trihydroxy-16S-methyl-18,19,20-trinor-17-(5'-methyl-2'-furyl)-prosta-5,13-dienoic acid methyl ester 11,15-bis THP ether.

The product was dissolved in 3 ml of dry benzene and 1 ml of dry DMSO, and then reacted with 0.144 g of DCC with some drops of pyridinium trifluoro acetate solution (0.6 ml of pyridine and 0.25 ml of trifluoro acetic acid) and pyridine, as catalyst.

The reaction mixture was warmed to 35° C. for 1 hour under stirring, diluted with 25 ml of benzene, and then 2 ml of 6% NaH$_2$PO$_4$ aqueous solution were added. The slurry was filtered and the solid was washed with 5 ml of benzene; the organic phase was separated, washed with 2 ml of water for four times, then dried, and the solvent was removed in vacuum to yield 0.250 g of crude 5Z,13E-9-oxo-11α,15S-dihydroxy-16S-methyl-18,19,20-trinor-17-(5'-methyl-2'-furyl)-prosta-5,13-dienoic acid methyl ester, 11,15-bis THP ether.

The crude was dissolved in a 4:2:1 mixture of acetic acid, water and THF (4 ml) and stirred at 40° C. for 3 hours; the mixture was quenched with 50 ml of ice and water and was extracted four times with 20 ml of ethyl acetate.

The organic phase was washed with 10 ml of 5% NaHCO$_3$ aqueous solution, water (10 ml) and then dried; the solvent was removed in vacuum and the crude was chromatographed on silica gel to yield 0.128 g of pure 5Z,13E-9-oxo-11α,15S-dihydroxy-16S-methyl-18,19,20-trinor-17-(5'-methyl-2'-furyl)-prosta-5,13-dienoic acid methyl ester, $[\alpha]_D = -59.2°$ (C=1, CHCl$_3$).

EXAMPLE 6

To a solution of 13E-9α,11α,15S-trihydroxy-16S-methyl-18,19,20-trinor-17-(2'-furyl)-prosta-13-enoic acid 11,15-bis THP ether (0.53 g) in 4.5 ml of dry benzene and 1.5 ml of dry DMSO, 0.285 g of DCC with some drops of pyridinium trifluoro acetate solution (obtained from 0.6 ml of pyridine and 0.25 ml of trifluoroacetic acid) and pyridine, as catalyst, were added. The reaction mixture was warmed to 30° C. for 1 hour under stirring, diluted with 20 ml of benzene and then 5 ml of 6% NaH$_2$PO$_4$ aqueous solution were added. The slurry was filtered and the solid was washed with 20 ml of benzene; the organic phase was separated, washed with water, dried and the solvent was removed in vacuum to yield 0.640 g of a yellow oil. The crude was chromatographed on silica gel column using ethylacetate:n-hexane and some drops of triethylamine as eluant to give 0.480 g of 13E-9-oxo-11α,15S-dihydroxy-16S-methyl-18,19,20-trinor-17-(2'-furyl)-prosta-13-enoic acid 11,15-bis-THP ether as a clear oil, $[\alpha]_D = -85°$ (C=1, CHCl$_3$). The product was dissolved in 2:1 mixture of acetic acid and water (10 ml) and stirred at 40° C. for 3 hours. The mixture was quenched with 50 ml of ice and water, and was extracted four times with 20 ml of ethylacetate. The organic phase was washed with water, dried and the solvent was distilled in vacuum. The crude was chromatographed on silica gel column using ethyl acetate:n-hexane 8:2 as eluant to give 0.230 g of pure 13E-9-oxo-11α,15S-dihydroxy-16S-methyl-18,19,20-trinor-17-(2'-furyl)-prosta-13-enoic acid as oil, $[\alpha]_D = -53°$ (C=1, EtOH). Following the same procedure the epimeric 13E-9-oxo-11α,15R-dihydroxy-16S-methyl-18,19,20-trinor-17-(2'-furyl)-prosta-13-enoic acid was prepared, $[\alpha]_D = -72°$ (C=1, EtOH).

By analogous procedure the following compounds were obtained, wherein the $[\alpha]_D$ values are for C=1 concentrations in ethanol:

5Z,13E-9-oxo-11α,15S-dihydroxy-16S-methyl-18,19,20-trinor-17-(2'-furyl)-prosta-5,13-dienoic acid, $[\alpha]_D = -54°$;

5Z,13E-9-oxo-11α,15S-dihydroxy-16S-methyl-18,19,20-trinor-17-(3'-furyl)-prosta-5,13-dienoic acid, $[\alpha]_D = -55.4°$;

5Z,13E-9-oxo-11α,15S-dihydroxy-16S-ethyl-18,19,20-trinor-17-(2'-furyl)-prosta-5,13-dienoic acid, $[\alpha]_D = -53.8°$;

5Z,13E-9-oxo-11α,15S-dihydroxy-16S-ethyl-18,19,20-trinor-17-(3'-furyl)-prosta-5,13-dienoic acid, $[\alpha]_D = -56°$;

5Z,13E-9-oxo-11α,15S-dihydroxy-16S-methyl-18,19,20-trinor-17-(5'-methyl-2'-furyl)-prosta-5,13-dienoic acid, $[\alpha]_D = -61°$;

5Z,13E-9-oxo-11α,15S-dihydroxy-16S-ethyl-18,19,20-trinor-17-(5'-methyl-2'-furyl)-prosta-5,13-dienoic acid, $[\alpha]_D = -60.4°$;

5Z,13E-9-oxo-11α,15S-dihydroxy-16S-methyl-18,19,20-trinor-17-(5'-ethyl-2'-furyl)-prosta-5,13-dienoic acid, $[\alpha]_D = -68°$;

13E-9-oxo-11α,15S-dihydroxy-16S-methyl-18,19,20-trinor-17-(3'-furyl)-prosta-13-enoic acid, $[\alpha]_D = -56°$;

13E-9-oxo-11S,15S-dihydroxy-16S-ethyl-18,19,20-trinor-17-(2'-furyl)-prosta-13-enoic acid, $[\alpha]_D = -50°$;

13E-9-oxo-11α,15S-dihydroxy-16S-ethyl-18,19,20-trinor-17-(3'-furyl)-prosta-13-enoic acid, $[\alpha]_D = -58°$;

13E-9-oxo-11α,15S-dihydroxy-16S-methyl-18,19,20-trinor-17-(5'-methyl-2'-furyl)-prosta-13-enoic acid, $[\alpha]_D = -60.5°$;

13E-9-oxo-11α,15S-dihydroxy-16S-ethyl-18,19,20-trinor-17-(5'-methyl-2'-furyl)-prosta-13-enoic acid, $[\alpha]_D = -64°$;

13E-9-oxo-11α,15S-dihydroxy-16S-methyl-18,19,20-trinor-17-(5'-ethyl-2'-furyl)-prosta-13-enoic acid, $[\alpha]_D = -68.7°$; and the 15R and 16R-epimers of all the above listed compounds, in particular:

13E-9-oxo-11α,15S-dihydroxy-16R-methyl-18,19,20-trinor-17-(2'-furyl)-prosta-13-enoic acid, $[\alpha]_D = -68.5°$, and 5Z,13E-9-oxo-11α,15S-dihydroxy-16R-methyl-18,19,20-trinor-17-(B 2'-furyl)-prosta-5,13-dienoic acid, $[\alpha]_D = -71°$.

EXAMPLE 7

A solution of dimethyl {[2-oxo-3S-3-methyl-4-(2-furyl)]-butyl}phosphonate (5.00 g) in 40 ml of dry benzene was dropped into a stirred suspension of 0.576 g of NaH (dispersion in mineral oil) in 100 ml of dry benzene, under a nitrogen atmosphere and with exclusion of moisture. The temperature was maintained at about 20°–25° C. and the yellow-orange solution was stirred until the evolution of hydrogen had stopped; a solution of [(2β-formyl-3α,5α-dihydroxy-3-benzoate)-cyclopent-1α-yl]-acetic acid-γ-lactone (7.95 g) in 100 ml of dry benzene was then added at once.

The mixture was stirred for 60 minutes and then diluted with 100 ml of 6% (w/v) aqueous $NaH_2PO_4$ solution; the organic phase was separated, washed until neutral with brine, dried, and the solvent was removed by evaporation.

The crude product (11.83 g) was purified by chromatography on silica gel column using as eluant phase ethyl acetate:n-hexane 6:4. Pure 1α-{[2β-(3-oxo-4S-4-methyl-5-(2-furyl)-pent-1E-enyl)-3α,5α-dihydroxy-3-benzoate]-cyclopent1-yl}-acetic acid-γ-lactone (7.91 g) was so obtained as oil, $[α]_D = -67.17°$ (C=1, $CHCl_3$).

By proceeding in analogous way the following derivatives were prepared:

1α-{[2β-(3-oxo-4S-4-methyl-6-(2-furyl)-hex-1E-enyl)-3α,5α-dihydroxy-3-benzoate]-cyclopent-1-yl}-acetic acid-γ-lactone;

1α-{[2β-(3-oxo-4S-4-ethyl-6-(2-furyl)-pent-1E-enyl)-3α,5α-dihydroxy-3-benzoate]-cyclopent-1-yl}-acetic acid-γ-lactone;

1α-{[2β-(3-oxo-4S-4-ethyl-6-(2-furyl)-hex-1E-enyl)-3α,-5α-dihydroxy-3-benzoate]-cyclopent-1-yl}-acetic acid-γ-lactone;

1α-{[2β-(3-oxo-4S-4-methyl-5-(2-furyl-5-methyl)-pent-1E-enyl)-3α,5α-dihydroxy-3-benzoate]-cyclopent-1-yl}-acetic acid-γ-lactone;

1α-{[2β-(3-oxo-4S-4-ethyl-5-(2-furyl-5-methyl)-pent-1E-enyl)-3α,5α-dihydroxy-3-benzoate]-cyclopent-1-yl}-acetic acid-γ-lactone, and the corresponding 4R epimers.

EXAMPLE 8

Sodium boro hydride (1.751 g) was added under stirring to 160 ml of methanol cooled to −30° C. with external cooling-bath. After complete dissolution, a solution of 1α-{[2β-(3-oxo-4S-4-methyl-5-(2-furyl)-pent-1E-enyl)-3α,5α-dihydroxy-3-benzoate]-cyclopent-1-yl}-acetic acid-γ-lactone (7.00 g) in 60 ml of methanol cooled to −5° to −10° C. was dropped into the mixture in about 30 minutes; the internal vessel's temperature was kept at −25° C.

After stirring for 30 minutes at that temperature the excess of the reagent was destroyed by addition of 4 ml of acetic acid; the mixture was left to rise to room temperature and then the solvent was evaporated in vacuo.

The residue was taken up with ethyl acetate:water (250:80), and the reaction mixture was stirred for 1 hour; the aqueous layer was extracted with ethyl acetate and the collected organic phases washed until neutral with 5% $NaHCO_3$ aqueous solution, then with brine and evaporated to dryness.

The crude product, a mixture of the two epimeric alcohols, was chromatographed on silica gel column using a preparative HPLC apparatus with methylene chloride:ethyl acetate:methanol 80:20:1 as eluant phase so obtaining 3.42 g of pure less polar, fast moving epimar 1α-{[2β-(3S,4S-3-hydroxy-4-methyl-5-(2-furyl)-pent-1E-enyl)-3α,5α-dihydroxy-3-benzoate]-cyclopent-1-yl}-acetic acid-γ-lactone, $[α]_D = -60.04°$ (C=1, $CHCl_3$), and 2.96 g of pure more polar epimer 1α-{[2β-(3R,4S-3-hydroxy-4-methyl-5-(2-furyl)-pent-1E-enyl)-3α,5α-dihydroxy-3-benzoate]-cyclopent-1-yl}-acetic acid-γ-lactone, $[α]_D = -91.3°$ (C=1, $CHCl_3$).

EXAMPLE 9

The 1α-{[2β-(3S,4S-3-hydroxy-4-methyl-5-(2-furyl)-pent-1E-enyl)-3α,5α-dihydroxy-3-benzoate]-cyclopent-1-yl}-acetic acid-γ-lactone (1.10 g) was dissolved in 100 ml of dry methanol and then treated with 0.42 g of powdered dry $K_2CO_3$ and the mixture was stirred at room temperature for 2 hours.

The salts, which precipitated, were removed by filtration and the filtrate, concentrated in vacuo to a small volume, was taken up with 200 ml of 30% $NaH_2PO_4$ aqueous solution, extracted three times with 50 ml of ethyl acetate and the solvent was removed in vacuo to give 1.14 g of crude oily 1α-{[2β-(3S,4S-3-hydroxy-4-methyl-5-(2-furyl)-pent-1E-enyl)-3α,5α-dihydroxy]-cyclopent-1-yl}-acetic acid-γ-lactone.

A solution of this product in 20 ml of dry methylene chloride was reacted with 0.541 g of dihydropyran and 6 mg of anhydrous p-toluenesulfonic acid and stirred for 1 hour at room temperature.

The reaction mixture was treated with 0.1 ml of pyridine, diluted with diethyl ether (60 ml) then washed with 5% $NaHCO_3$ aqueous solution and water until neutral. The solvent was removed to give 1.62 g of crude product which was transferred to a silica gel column and chromatografed with ethyl acetate:n-hexane:triethylamine 50:50:0.1 as eluant to yield 1.47 g of pure 1α-{[2β-(3S,4S-3-hydroxy-4-methyl-5-(2-furyl)-pent-1E-enyl)-3α,5α-dihydroxy]-cyclopent-1-yl}-acetic acid-γ-lactone-3,3α-bis THP ether.

EXAMPLE 10

A solution of 1.04 g of 1α-{[2β-(3S,4S-3-hydroxy-4-methyl-5-(2-furyl)-pent-1E-enyl)-3α,5α-dihydroxy-3-benzoate]-cyclopent-1-yl}-acetic acid-γ-lactone in 20 ml of re-distilled methylene chloride was reacted with 1.026 g of thriethylamine and 0.551 g of trimethylchlorosilane using 15 mg of 4-dimethylamino pyridine as catalyst. The mixture was stirred at room temperature for 30 minutes then diluted with 40 ml of n-hexane; the salts, which precipitated were filtered off and the filtrate was washed with buffered pH 7.5 aqueous solution. The solvent was removed in vacuo to give 1.23 g of oily 1α-{[2β-(3S,4S-3-hydroxy-4-methyl-5-(2-furyl)-pent-1E-enyl)-3α-5α-dihydroxy-3α-benzoate]-cyclopent-1-yl}-acetic acid-γ-lactone-3-trimethylsilyl ether.

EXAMPLE 11

A 1.2M solution of DIBAH (2.82 ml) in toluene was added over a period of 20 minutes to a stirred solution of 1α-{[2β-(3S,4S-3-hydroxy-4-methyl-5-(2-furyl)-pent-1E-enyl)-3α,5α-dihydroxy]-cyclopent-1-yl}-acetic acid-γ-lactone, 3,3α-bis THP ether (1.07 g) in 20 ml of dry toluene, cooled to −60° C. with external cooling bath. Stirring was continued for 30 minutes, then the reaction mixture was treated with 1 ml of ethyl acetate and after ,10 minutes warmed to 0°-2° C. and treated with 1 ml of water, 2 g of anhydrous sodium sulfate and 2.5 g of Celite ®, then filtered. The filtrate was evaporated to dryness under vacuum to give 1.37 g of 1α-{[2β-(3S,4S-3-hydroxy-4-methyl-5-(2-furyl)-pent-1E-enyl)-3α,5α-dihydroxy]-cyclopent-1-yl}-acetaldehyde-γ-hemiacetal 3,3α-bis THP ether.

EXAMPLE 12

To a solution of 1α-{[2β-(3S,4S-3-hydroxy-4-methyl-5-(2-furyl-pent-1E-enyl)-3α,5α-dihydroxy-3-benzoate]-cyclopent-1-yl}-acetic acid-γ-lactone-3-trimethylsilyl ether (1.23 g) in 15 ml of dry toluene, cooled to −65° C., 6.35 ml of 1.2M DIBAH in toluene were added dropwise under nitrogen atmosphere in 10 minutes cooling the mixture between −65° C. and −70° C.

The reaction mixture was stirred for 30 minutes then ethylacetate (2 ml) was added; after 10 minutes the solution was warmed to 0°-2° C. and 1 ml of water was dropped into the mixture.

Stirring was continued for 1 hour then 2 g of anhydrous sodium sulfate and 2.5 g of Celite ® were added. The solid was filtered off and the filtrate was evaporated to dryness under vacuum to yield 1.30 g of an oil which was purified by silica gel flash chromatography with ethyl acetate:n-hexane:triethylamine 90:10:0.2 as eluant to give 0.830 g of pure 1α-{[2β-(3S,4S-3-hydroxy-4-methyl-5-(2-furyl)-pent-1E-enyl)-3α,5α-dihydroxy]-cyclopent-1-yl}-acetaldehyde-γ-hemiacetal-3-trimethylsilyl ether.

EXAMPLE 13

Under a nitrogen atmosphere, to a solution of 1.514 g of potassium tert-butoxide in 15 ml of dry DMSO, stirring and cooling to 20° C., 2.990 g of crystalline triphenyl (4-carboxybutyl)-phosphonium bromide were added portionwise and the stirring was continued until this compound was completely dissolved.

The deep orange-red solution of the ylide was then treated with 1α-{[2β-(3S,4S-3-hydroxy-4-methyl-5-(2-furyl)-pent-1E-enyl)-3α,5α-dihydroxy]-cyclopent-1-yl}acetaldehyde-γ-hemiacetal-3,3α-bis THP ether (1.37 g) in 7 ml of dry DMSO. After stirring for 15 minutes at room temperature the reaction mixture was quenched with 200 ml of iced water; the solution was extracted with 50 ml of diethyl ether, which was discarded; the aqueous phase was acidified to pH 5.5 and extracted several times with diethyl ether:n-pentane 1:1 by volume. The combined organic extracts were washed with saturated $(NH_4)_2SO_4$ aqueous solution, dried on $Na_2SO_4$ and evaporated to dryness, to give 1.65 g of crude 5Z,13E-9α,11α,15S-trihydroxy-16S-methyl-18,19,20-trinor-17-(2′-furyl)-prosta-5,13-dienoic acid-11,15-bis-THP ether. The product was de-protected at the 11 and 15 positions by treatment with aqueous acetic acid following the procedure described in example 5, to give 5Z,13E-9α,11α,15S-trihydroxy-16S-methyl-18,19,20-trinor-17-(2′-furyl)-prosta-5,13-dienoic acid, $[\alpha]_D = +28.2°$ (C=1, ethanol).

EXAMPLE 14

A solution of 1.65 g of 5Z,13E-9α,11α,15S-trihydroxy-16S-methyl-18,19,20-trinor-17-(2′-furyl)-prosta-5,13-dienoic acid 11,15-bis THP ether in 20 ml of diethyl ether was reacted with a 1N solution of diazomethane until persistent yellow colour. The solvent was removed in vacuum yielding 1.67 g of crude methyl ester. This was purified by silica gel chromatography eluting with ethyl acetate:n-hexane:triethylamine 50:50:0.1 to give 1.48 g of pure 5Z,13E-9α,11α,15S-trihydroxy-16S-methyl-18,19,20-trinor-17-(2′-furyl)-prosta-5,13-dienoic acid methyl ester 11,15-bis THP ether, $[\alpha]_D = +36.2°$ (C=1, CHCl$_3$).

The 11,15-bis THP ether protecting groups were removed by treatment with aqueous acetic acid according to the procedure described in example 5, so obtaining 5Z,13E-9α,11α,15S-trihydroxy-16S-methyl-18,19,20-trinor-17-(2′-furyl)-prosta-5,13-dienoic acid methyl ester, $[\alpha]_D = +25.04°$ (C=1, ethanol).

EXAMPLE 15

A solution of 5Z,13E-9α,11α,15S-trihydroxy-16S-methyl-18,19,20-trinor-17-(2′-furyl)-prosta-5,13-dienoic acid methyl ester 11,15-bis THP ether (1.12 g) in 20 ml of acetone was cooled to −25° C. and then treated with 1.279 ml of Jones' reagent, added over 10 minutes maintaining the temperature between −25° and −30° C.

The reaction mixture was allowed to warm up to −10° C. and kept for 30 minutes at that temperature. After destroying the excess of Jones' reagent with the addition of 1 ml of isopropanol, the mixture was diluted with 60 ml of benzene; the organic phase was repeatedly washed with saturated $(NH_4)_2SO_4$ aqueous solution until neutral, dried, and evaporated to dryness, yielding 1.0 g of crude 5Z,13E-9-oxo,11α,15S-dihydrox-16S-methyl-18,19,20-trinor-17-(2′-furyl)-prosta-5,13-dienoic acid methyl ester 11,15-bis THP ether.

A solution of this crude in 4 ml of glacial acetic acid and 2 ml of water was warmed to 40° C. for 90 minutes then quenched with 100 ml of iced water, extracted with 200 ml of ethyl acetate, and the organic phase was washed with 5% $N_aHCO_3$ aqueous solution and water.

The solvent was removed in vacuum and the crude was chromatographed on silica gel column using ethyl acetate: n-hexane 8:2 to give 0.337 g of pure 5Z,13E-9-oxo,11α,15S-dihydroxy-16S-methyl-18,19,20-trinor-17-(2′furyl)-prosta-5,13-dienoic acid methyl ester, $[\alpha]_D = -53.4°$, $[\alpha]_{365} = -334.3°$ (C=1, ethanol 95°); NMR (CDCl$_3$) δppm: 0.87 (3H, d; CH$_3$–C$_{17}$); 5.35 (2H, m; Δ5,6); 5.60 (2H, m; Δ13,14); 6.00, 6.27, 7.28 (3H; furyl).

By analogous procedure the following compounds were prepared, wherein the $[\alpha]_D$ values are for C=1 concentrations in ethanol:

5Z,13E-9-oxo-11α,15S-dihydroxy-16S-methyl-18,19,20-trinor-17-(3′-furyl)-prosta-5,13-dienoic acid methyl ester, $[\alpha]_D = -52°$;

5Z,13E-9-oxo-11α,15S-dihydroxy-16S-ethyl-18,19,20-trinor-17-(2′-furyl)-prosta-5,13-dienoic acid methyl ester, $[\alpha_D = -53°$;

5Z,13E-9-oxo-11α,15S-dihydroxy-16S-ethyl-18,19,20-trinor-17-(3′-furyl)-prosta-5,13-dienoic acid methyl ester, $[\alpha]_D = -52.5°$;

5Z,13E-9-oxo-11α,15S-dihydroxy-16S-methyl-18,19,20-trinor-17-(5′-methyl-2′-furyl)-prosta-5,13-dienoic acid methyl ester, $[\alpha]_D = -59.2°$;

5Z,13E-9-oxo-11α,15S-dihydroxy-16S-ethyl-18,19,20-trinor-17-(5′-methyl-2′-furyl)-prosta-5,13-dienoic acid methyl ester, $[\alpha]_D = -57°$;

5Z,13E-9-oxo-11α,15S-dihydroxy-16S-methyl-18,19,20-trinor-17-(5′-ethyl-2′-furyl)-prosta-5,13-dienoic acid methyl ester, $[\alpha]_D = -67°$;

5Z,13E-9-oxo-11α,15S-dihydroxy-16R-methyl-18,19,20-trinor-17-(2′-furyl)-prosta-5,13-dienoic acid methyl ester, $[\alpha]_D = -65°$;

13E-9-oxo-11α,15S-dihydroxy-16S-methyl-18,19,20-trinor-17-(2′-furyl)-prosta-13-enoic acid methyl ester, $[\alpha]_D = -51.8°$;

13E-9-oxo-11α,15S-dihydroxy-16S-methyl-18,19,20-trinor-17-(3′-furyl)-prosta-13-enoic acid methyl ester, $[\alpha]_D = -54°$;

13E-9-oxo-11α,15S-dihydroxy-16S-methyl-18,19,20-trinor-17-(5′-methyl-2′-furyl)-prosta-13-enoic acid methyl ester, $[\alpha]_D = -59°$, and the corresponding 15R and 16R epimers.

EXAMPLE 16

A solution of 0.830 g of 1α-{[2β-(3S,4S-3-hydroxy-4-methyl-5-(2-furyl)-pent-1E-enyl)-3α,5α-dihydroxy]-cyclopent-1-yl}-acetaldehyde-γ-hemiacetal-3-trimethylsilyl ether in 5 ml of dry DMSO was reacted with a solution of the ylide obtained as follows: under nitrogen atmosphere, a suspension of 80% $N_aH$ (dispersion in mineral oil) (0.395 g) in dry DMSO (15 ml) was heated under stirring at 60° C. until evolution of hydrogen ceased and the formed sodium methylsulphinyl methide was reacted with 2.913 g of triphenyl-(4-carboxybutyl)-phosphonium bromide.

The reaction mixture was cooled to 20° C. and stirred for 20 minutes under nitrogen atmosphere, then it was dropped into 150 ml of ice/water mixture.

The alkaline phase was extracted with diethyl ether to remove the triphenylphosphineoxide and the ethereal extract was washed with 0.5N NaOH and then discarded. The alkaline phases were combined, acidified to pH 5.9 with 30% $NaH_2PO_4$ aqueous solution and extracted several times with diethyl ether.

The combined organic extracts were washed with saturated $(NH_4)_2SO_4$ aqueous solution, dried on $Na_2SO_4$ and evaporated to dryness to give 1.03 g of 5Z,13E-9α,11α,15S-trihydroxy-16S-methyl-18,19,20-trinor-17-(2'furyl)-prosta-5,13-dienoic acid, $[\alpha]_D=+28.2°$ (C=1, ethanol).

The free acid (0.5 g) was dissolved in 8 ml of diethyl ether and esterified following the procedure described in the example 14 to give, after chromatographic purification on silica gel using methylene chloride: methanol 9:1 as eluant, 0.41 g of pure 5Z,13E-9α,11α,15S-trihydroxy-16S-methyl-18,19,20-trinor-17-(2'-furyl)-prosta-5,13-dienoic acid methyl ester, $[\alpha]_D=+25.12°$; $[\alpha]_{365}=+77.52°$ (C=1, ethanol).

Following analogous procedure the following derivatives were obtained:

5Z,13E,9α,11α,15S-trihydroxy-16S-methyl-18,19,20-trinor-17-(3'-furyl)-prosta-5,13-dienoic acid methyl ester, $[\alpha]_D=+26°$;

5Z,13E-9α,11α,15S-trihydroxy-16S-ethyl-18,19,20-trinor-17-(2'-furyl)-prosta-5,13-dienoic acid methyl ester, $[\alpha]_D=+27.5°$;

5Z,13E-9α,11α,15S-trihydroxy-16S-ethyl-18,19,20-trinor-17-(3'-furyl)-prosta-5,13-dienoic acid methyl ester, $[\alpha]_D=+26.8°$;

5Z,13E-9α,11α,15S-trihydroxy-16S-methyl-18,19,20-trinor-17-(5'-methyl-2'-furyl)-prosta-5,13-dienoic acid methyl ester, $[\alpha]_D=+27.2°$;

5Z,13E-9α,11α,15S-trihydroxy-16S-ethyl-18,19,20-trinor-17-(5'-methyl-2'-furyl)-prosta-5,13-dienoic acid methyl ester, $[\alpha]_D=+26°$;

5Z,13E-9α,11α,15S-trihydroxy-16S-methyl-18,19,20-trinor-17-(5'-ethyl-2'-furyl)-prosta-5,13-dienoic acid methyl ester, $[\alpha]_D=+30°$;

and the 15R and 16R epimers of all the above listed compounds.

EXAMPLE 17

To a solution of 1.373 g of dicyclohexylcarbodiimide (DCC) in 0.661 g of 2-ethoxy-ethanol, cooled to 0° C., 0.017 g of $C_uCl$ were added; the mixture was stirred for about 1 hour ad 0° C. then it was allowed to rise to the room temperature and stirred at this temperature for 24 hours.

The mixture was then diluted with n-hexane (5 ml), filtered on silica gel and washed with n-hexane. The solvent was removed to obtain 1.00 g pure dicyclohexyl-2-ethoxy-ethyl isourea which was dissolved in 10 ml of THF and then added to a solution of 5Z,13E-9α,1-1α,15S-trihydroxy-16S-methyl-18,19,20-trinor-17-(2'-furyl)-prosta-5,13-dienoic acid (1 g) in 10 ml of dry THF. The mixture was warmed to 60° C. and kept at this temperature for 6 hours. The solvent was removed under vacuum and the crude product thus obtained was purified on silica gel usign a mixture of ethyl acetate and n-hexane (70:30) as eluant. Pure 5Z,13E-9α,11α,15S-trihydroxy-16S-methyl-18,19,20-trinor-17-(2'-furyl)-prosta-5,13-dienoic acid 2-ethoxy-ethyl ester (0.856 g) was collected, $[\alpha]_D=+19.6°$ (C=1, $CHCl_3$).

By analogous procedure the following esters were obtained, wherein the $[\alpha]_D$ values are for C=1 concentrations in $CHCl_3$:

5Z,13E-9α,11α,15S-trihydroxy-16S-methyl-18,19,20-trinor-17-(3'-furyl)-prosta-5,13-dienoic acid 2-ethoxy-ethyl ester, $[\alpha]_D=+23°$;

5Z,13E-9α,11α,15S-trihydroxy-16S-ethyl-18,19,20-trinor-17-(2'-furyl)-prosta-5,13-dienoic acid 2-ethoxy-ethyl ester, $[\alpha]_D=+20.5°$;

5Z,13E-9α,11α,15S-trihydroxy-16S-ethyl-18,19,20-trinor-17-(3'-furyl)-prosta-5,13-dienoic acid 2-ethoxy-ethyl ester, $[\alpha]_D=+22°$;

5Z,13E-9α,11α,15S-trihydroxy-16S-methyl-18,19,20-trinor-17-(5'-methyl-2'-furyl)-prosta-5,13-dienoic acid 2-ethoxy-ethyl ester, $[\alpha]_D=+24.5°$;

5Z,13E-9α,11α,15S-trihydroxy-16S-ethyl-18,19,20-trinor-17-(5'-methyl-2'-furyl)-prosta-5,13-dienoic acid 2-ethoxy-ethyl ester, $[\alpha]_D=+25.9°$;

5Z,13E-9α,11α,15S-trihydroxy-16S-methyl-18,19,20-trinor-17-(5'-ethyl-2'-furyl)-prosta-5,13-dienoic acid 2-ethoxy-ethyl ester, $[\alpha]_D=+27°$;

5Z,13E-9α,11α,15S-trihydroxy-16S-methyl-18,19,20-trinor-17-(2'-furyl)-prosta-5,13-dienoic acid ester, $[\alpha]_D=+25°$;

5Z,13E-9α,11α,15S-trihydroxy-16S-methyl-18,19,20-trinor-17-(3'-furyl)-prosta-5,13-dienoic acid ethyl ester, $[\alpha]_D=+26°$;

5Z,13E-9α,11α,15S-trihydroxy-16S-ethyl-18,19,20-trinor-17-(2'-furyl)-prosta-5,13-dienoic acid ethyl ester, $[\alpha]_D=+26.9°$;

5Z,13E-9α,11α,15S-trihydroxy-16S-ethyl-18,19,20-trinor-17-(3'-furyl)-prosta-5,13-dienoic acid ethyl ester, $[\alpha]_D=+20°$;

5Z,13E-9α,11α,15S-trihydroxy-16S-methyl-18,19,20-trinor-17-(5'-methyl-2'-furyl)-prosta-5,13-dienoic acid ethyl ester, $[\alpha]_D=+28°$;

5Z,13E-9α,11α,15S-trihydroxy-16S-ethyl-18,19,20-trinor-17-(5'-methyl-2'-furyl)-prosta-5,13-dienoic acid ethyl ester, $[\alpha]_D=+28.4°$;

5Z,13E-9α,11α,15S-trihydroxy-16S-methyl-18,19,20-trinor-17-(5'-ethyl-2'-furyl)-prosta-5,13-dienoic acid ethyl ester, $[\alpha]_D=+30.2°$;

5Z,13E-9α,11α,15S-trihydroxy-16S-methyl-18,19,20-trinor-17-(2'-furyl)-prosta-5,13-dienoic acid morpholino ethyl ester, $[\alpha]_D=+20.5°$;

5Z,13E-9α,11α,15S-trihydroxy-16S-methyl-18,19,20-trinor-17-(3'-furyl)-prosta-5,13-dienoic acid morpholino ethyl ester, $[\alpha]_D=+18.7°$;

5Z,13E-9α,11α,15S-trihydroxy-16S-ethyl-18,19,20-trinor-17-(2'-furyl)-prosta-5,13-dienoic acid morpholino ethyl ester, $[\alpha]_D=+21°$;

5Z,13E-9α,11α,15S-trihydroxy-16S-ethyl-18,19,20-trinor-17-(3'-furyl)-prosta-5,13-dienoic acid morpholino ethyl ester, $[\alpha]_D=+22.7°$;

5Z,13E-9α,11α,15S-trihydroxy-16S-methyl-18,19,20-trinor-17-(5'-methyl-2'-furyl)-prosta-5,13-dienoic acid morpholino ethyl ester, $[\alpha]_D = +24.2°$;
5Z,13E-9α,11α,15S-trihydroxy-16S-ethyl-18,19,20-trinor-17-(5'-methyl-2'-furyl)-prosta-5,13-dienoic acid morpholino ethyl ester, $[\alpha]_D = +23°$;
5Z,13E-9α,11α,15S-trihydroxy-16S-methyl-18,19,20-trinor-17-(5'-ethyl-2'-furyl)-prosta-5,13-dienoic acid morpholino ethyl ester, $[\alpha]_D = +21.8°$;
5Z,13E-9-oxo-11α,15S-dihydroxy-16S-methyl-18,19,20-trinor-17-(2'-furyl)-prosta-5,13-dienoic acid 2-ethoxyethyl ester, $[\alpha]_D = -50.7°$;
5Z,13E-9-oxo-11α,15S-dihydroxy-16S-methyl-18,19,20-trinor-17-(3'-furyl)-prosta-5,13-dienoic acid 2-ethoxy-ethyl ester, $[\alpha]_D = -47.8°$;
5Z,13E-9-oxo-11α,15S-dihydroxy-16S-ethyl-18,19,20-trinor-17-(2'-furyl)-prosta-5,13-dienoic acid 2-ethoxy-ethyl ester, $[\alpha]_D = -52.4°$;
5Z,13E-9-oxo-11α,15S-dihydroxy-16S-ethyl-18,19,20-trinor-17-(3'-furyl)-prosta-5,13-dienoic acid 2-ethoxy-ethyl ester, $[\alpha]_D = -51°$;
5Z,13E-9-oxo-11α,15S-dihydroxy-16S-methyl-18,19,20-trinor-17-(5'-methyl-2'-furyl)-prosta-5,13-dienoic acid 2-ethoxy-ethyl ester, $[\alpha]_D = -55.4°$;
5Z,13E-9-oxo-11α,15S-dihydroxy-16S-ethyl-18,19,20-trinor-17-(5'-methyl-2'-furyl)-prosta-5,13-dienoic acid 2-ethoxy-ethyl ester, $[\alpha]_D = -54°$;
5Z,13E-9-oxo-11α,15S-dihydroxy-16S-methyl-18,19,20-trinor-17-(5'-ethyl-2'-furyl)-prosta-5,13-dienoic acid 2-ethoxy-ethyl ester, $[\alpha]_D = -53.4°$;
5Z,13E-9-oxo-11α,15S-dihydroxy-16S-methyl-18,19,20-trinor-17-(2'-furyl)-prosta-5,13-dienoic acid ethyl ester, $[\alpha]_D = -53.7°$;
5Z,13E-9-oxo-11α,15S-dihydroxy-16S-methyl-18,19,20-trinor-17-(3'-furyl)-prosta-5,13-dienoic acid ethyl ester, $[\alpha]_D = -51.9°$;
5Z,13E-9-oxo-11α,15S-dihydroxy-16S-ethyl-18,19,20-trinor-17-(2'-furyl)-prosta-5,13-dienoic acid ethyl ester, $[\alpha]_D = -52°$;
5Z,13E-9-oxo-11α,15S-dihydroxy-16S-ethyl-18,19,20-trinor-17-(3'-furyl)-prosta-5,13-dienoic acid ethyl ester, $[\alpha]_D = -50°$;
5Z,13E-9-oxo-11α,15S-dihydroxy-16S-methyl-18,19,20-trinor-17-(5'-methyl-2'-furyl)-prosta-5,13-dienoic acid ethyl ester, $[\alpha]_D = -60.5°$;
5Z,13E-9-oxo-11α,15S-dihydroxy-16S-ethyl-18,19,20-trinor-17-(5'-methyl-2'-furyl)-prosta-5,13-dienoic acid ethyl ester, $[\alpha]_D = -59.9°$;
5Z,13E-9-oxo-11α,15S-dihydroxy-16S-methyl-18,19,20-trinor-17-(5'-ethyl-2'-furyl)-prosta-5,13-dienoic acid ethyl ester, $[\alpha]_D = -72°$;
5Z,13E-9-oxo-11α,15S-dihydroxy-16S-methyl-18,19,20-trinor-17-(2'-furyl)-prosta-5,13-dienoic acid morpholino ethyl ester, $[\alpha]_D = -48.2°$;
5Z,13E-9-oxo-11α,15S-dihydroxy-16S-methyl-18,19,20-trinor-17-(3'-furyl)-prosta-5,13-dienoic acid morpholino ethyl ester, $[\alpha]_D = -48.8°$;
5Z,13E-9-oxo-11α,15S-dihydroxy-16S-ethyl-18,19,20-trinor-17-(2'-furyl)-prosta-5,13-dienoic acid morpholino ethyl ester, $[\alpha]_D = -47.9°$;
5Z,13E-9-oxo-11α,15S-dihydroxy-16S-ethyl-18,19,20-trinor-17-(3'-furyl)-prosta-5,13-dienoic acid morpholino ethyl ester, $[\alpha]_D = -45.6°$;
5Z,13E-9-oxo-11α,15S-dihydroxy-16S-methyl-18,19,20-trinor-17-(5'-methyl-2'-furyl)-prosta-5,13-dienoic acid morpholino ethyl ester, $[\alpha]_D = -40.7°$;
5Z,13E-9-oxo-11α,15S-dihydroxy-16S-ethyl-18,19,20-trinor-17-(5'-methyl-2'-furyl)-prosta-5,13-dienoic acid morpholino ethyl ester, $[\alpha]_D = -42.3°$;
5Z,13E-9-oxo-11α,15S-dihydroxy-16S-methyl-18,19,20-trinor-17-(5'-ethyl-2'-furyl)-prosta-5,13-dienoic acid morpholino ethyl ester, $[\alpha]_D = -45.75°$, and the corresponding 15R and 15R epimers.

EXAMPLE 18

A solution of 5Z,13E-9α,11α,15S-trihydroxy-16S-methyl-18,19,20-trinor-17-(2'-furyl)-prosta-5,13-dienoic acid methyl ester (0.73 g) in methyl alcohol (10 ml) was cooled with a cooling bath, and dry NH3 was bubbled into the solution until saturation.

The reaction vessel was closed and the mixture was maintained at room temperature for 24 hours then the ammonia was stripped with nitrogen and the methanol was removed.

The crude product was purified with preparative chromatographic HPLC technique on silica gel column using ethyl acetate: n-hexane (60:40) so obtaining pure 5Z,13E-9α,11α,15S-trihydroxy-16S-methyl-18,19,20-trinor-17-(2'-furyl)-prosta-5,13-dienoic acid amide (0.42 g), $[\alpha]_D = +31.2°$ (C=1, CHCl3).

The following analogous procedure the following amides were obtained.

5Z,13E-9α,11α,15S-trihydroxy-16S-methyl-18,19,20-trinor-17-(3'-furyl)-prosta-5,13-dienoic acid amide, $[\alpha]_D = +26.2°$;
5Z,13E-9α,11α,15S-trihydroxy-16S-ethyl-18,19,20-trinor-17-(2'-furyl)-prosta-5,13-dienoic acid amide, $[\alpha]_D = +27°$;
5Z,13E-9α,11α,15S-trihydroxy-16S-ethyl-18,19,20-trinor-17-(3'-furyl)-prosta-5,13-dienoic acid amide, $[\alpha]_D = +30°$;
5Z,13E-9α,11α,15S-trihydroxy-16S-methyl-18,19,20-trinor-17-(5'-methyl-2'-furyl)-prosta-5,13-dienoic acid amide, $[\alpha]_D = +32°$;
5Z,13E-9α,11α,15S-trihydroxy-16-S-ethyl-18,19,20-trinor-17-(5'-methyl-2'-furyl)-prosta-5,13-dienoic acid amide, $[\alpha]_D = +30.5°$;
5Z,13E-9α,11α,15S-trihydroxy-16S-methyl-18,19,20-trinor-17-(5'-ethyl-2'-furyl)-prosta-5,13-dienoic acid amide, $[\alpha]_D = +29.6°$, and the analogous 15R and 16R epimers.

EXAMPLE 19

A solution of 5Z,13E-9α,11α,15S-trihydroxy-16S-methyl-18,19,20-trinor-17-(2'-furyl)-prosta-5,13-dienoic acid (0.203 g) in 5 ml of ethanol was treated with 5 ml of 0.1N NaOH solution.

The alcohol was removed in vacuum and the aqueous solution was lyophilized to give 0.210 g of dry sodium salt of 5Z,13E-9α,11α,15S-trihydroxy-16S-methyl-18,19,20-trinor-17-(2'-furyl)-prosta-5,13-dienoic acid as white powder, $[\alpha]_D = +28.7°$ (C=1, ethanol).

By analogous method the following sodium salts were prepared:

5Z,13E-9α,11α,15S-trihydroxy-16S-methyl-18,19,20-trinor-17-(3'-furyl)-prosta-5,13-dienoic acid sodium salt;
5Z,13E-9α,11α,15S-trihydroxy-16S-ethyl-18,19,20-trinor-17-(2'-furyl)-prosta-5,13-dienoic acid sodium salt;
5Z,13E-9α,11α,15S-trihydroxy-16S-ethyl-18,19,20-trinor-17-(3'-furyl)-prosta-5,13-dienoic acid sodium salt;
5Z,13E-9α,11α,15S-trihydroxy-16S-methyl-18,19,20-trinor-17-(5'-methyl-2'-furyl)-prosta-5,13-dienoic acid sodium salt;

5Z,13E-9α,11α,15S-trihydroxy-16S-ethyl-18,19,20-trinor-17-(5'-methyl-2'-furyl)-prosta-5,13-dienoic acid sodium salt;

5Z,13E-9α,11α,15S-trihydroxy-16S-methyl-18,19,20-trinor-17-(5'-ethyl-2'-furyl)-prosta-5,13-dienoic acid sodium salt;

and the analogous 15R and 16R epimers.

EXAMPLE 20

A solution of 5Z,13E-9-oxo-11α,15S-dihydroxy-16S-methyl-18,19,20-trinor-17-(2'-furyl)-prosta-5,13-dienoic acid methyl ester (500 μg) in ethanol (6 ml) was sterilized by passage through a bacteria-retaining filter.

Portions of 0.1 ml were placed into 1 ml ampoules which were then sealed. The content of an ampoule was diluted with 1 ml of tris-HCl buffer solution having pH 8.6 to give a solution ready for administration by injection.

We claim:

1. An optically active or racemic compound of the following formula (I)

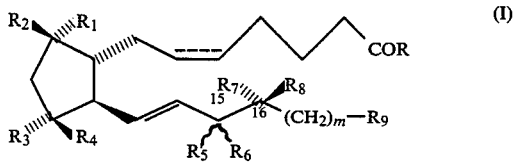

wherein
R is
(1) —OH or —OR' wherein R' is $C_1$–$C_6$ alkyl, or
(2)

wherein each of R" and R"' is, independently, hydrogen or $C_1$–$C_6$ alkyl;

one of $R_1$ and $R_2$ is hydrogen and the other is hydroxy, or $R_1$ and $R_2$, taken together, form an oxo group;

one of $R_3$ and $R_4$ is hydrogen and the other is hydroxy;

one of $R_5$ and $R_6$ is hydroxy and the other is hydrogen;

one of $R_7$ and $R_8$ is hydrogen and the other is a $C_1$–$C_4$ alkyl or tri-halo-$C_1$–$C_4$ alkyl group;

m is an integer of 1 to 3;

$R_9$ is a 2-furyl or 3-furyl group, optionally substituted by one or more substituents chosen from $C_1$–$C_4$ alkyl, $C_1$–$C_4$ alkoxy, tri-halo-$C_1$–$C_4$ alkyl and halogen; and the symbol $\rightleftharpoons$ represents a single bond or a cis double bond, and the pharmaceutically or veterinarily acceptable salts thereof.

2. A compound having the formula (I) reported above in claim 1,
wherein
R is hydroxy or OR' wherein R' is $C_1$–$C_6$ alkyl;

one of $R_1$ and $R_2$ is hydrogen and the other is hydroxy or $R_1$ and $R_2$, taken together, form an oxo group;

one of $R_3$ and $R_4$ is hydrogen and the other is hydroxy;

one of $R_5$ and $R_6$ is hydrogen and the other is hydroxy;

m is an integer of 1 to 3;

one of $R_7$ and $R_8$ is hydrogen and the other is $C_1$–$C_4$ alkyl;

$R_9$ is 2-furyl or 3-furyl optionally substituted by a $C_1$–$C_4$-alkyl or $C_1$–$C_4$ alkoxy or tri-halo-$C_1$–$C_4$-alkyl group, and the symbol $\rightleftharpoons$ represents a single bond or a cis-double bond; and the pharmaceutically or veterinarily acceptable salts thereof.

3. A compound having the formula (I) reported above in claim 1,
wherein
R is —OH or OR' wherein R' is $C_1$–$C_6$ alkyl;

one of $R_1$ and $R_2$ is hydrogen and the other is hydroxy or $R_1$ and $R_2$, taken together, form an oxo group;

one of $R_3$ and $R_4$ is hydrogen and the other is hydroxy;

one of $R_5$ and $R_6$ is hydrogen and the other is hydroxy;

m is 1;

one of $R_7$ and $R_8$ is hydrogen and the other is $C_1$–$C_4$ alkyl;

$R_9$ is unsubstituted 2-furyl, and the symbol $\rightleftharpoons$ represents a single bond or a cis-double bond; and the pharmaceutically or veterinarily acceptable salts thereof.

4. A compound selected from the group consisting of:
5Z,13E-9α,11α,15S-trihydroxy-16S-methyl-18,19,20-trinor-17-(2'-furyl)-prosta-5,13-dienoic acid;
5Z,13E-9α,11α,15S-trihydroxy-16R-methyl-18,19,20-trinor-17-(2'-furyl)-prosta-5,13-dienoic acid;
5Z,13E-9α,11α,15S-trihydroxy-16S-methyl-18,19,20-trinor-17-(3'-furyl)-prosta-5,13-dienoic acid;
5Z,13E-9α,11α,15S-trihydroxy-16R-methyl-18,19,20-trinor-17-(3'-furyl)-prosta-5,13-dienoic acid;
the $C_1$–$C_6$ alkyl esters thereof, and the pharmaceutically or veterinarily acceptable salts of the free acids.

5. A compound selected from the group consisting of:
5Z,13E-9-oxo-11α,15S-dihydroxy-16R-methyl-18,19,20-trinor-17-(2'-furyl)-prosta-5,13-dienoic acid;
13E-9-oxo-11α,15S-dihydroxy-16S-methyl-18,19,20-trinor-17-(2'-furyl)-prosta-13-enoic acid;
13E-9-oxo-11α,15S-dihydroxy-16R-methyl-18,19,20-trinor-17-(2'-furyl)-prosta-13-enoic acid;
the $C_1$–$C_6$ alkyl esters thereof, and the pharmaceutically or veterinarily acceptable salts of the free acids.

6. The compound 5Z,13E-9-oxo-11α,15S-dihydroxy-16S-methyl-18,19,20-trinor-17-(2'-furyl)-prosta-5,13-dienoic acid, and the $C_1$–$C_6$ alkyl esters thereof and the pharmaceutically or veterinarily acceptable salts thereof.

7. A $C_1$–$C_6$ alkyl ester of the compound of claim 6, wherein the ester is the methyl ester.

8. A pharmaceutical or veterinary composition suitable for use in inhibiting and preventing ulcers or as luteolytic agent, said composition comprising a therapeutically effective amount of a compound of claim 1 and a pharmaceutically or veterinarily acceptable carrier and/or diluent.

9. A method of inhibiting or preventing ulcers in a patient in need of it, said method comprising administering an effective amount of a compound of claim 1.

10. A method of inhibiting or preventing ulcers in a patient in need of it, said method comprising administering an effective amount of a composition of claim 8.

11. A method of producing luteolytic effect in a patient in need of it, said method comprising administering an effective amount of a compound of claim 1.

12. A method of producing luteolytic effect in a patient in need of it, said method comprising administering an effective amount of a composition of claim 8.

* * * * *